United States Patent
Traina

(10) Patent No.: US 12,144,537 B2
(45) Date of Patent: *Nov. 19, 2024

(54) END EFFECTOR INCLUDING WRIST ASSEMBLY AND ELECTROSURGICAL TOOL FOR ROBOTIC SURGICAL SYSTEMS

(71) Applicant: Covidien LP, Mansfield, MA (US)

(72) Inventor: Zachary Traina, Verona, NJ (US)

(73) Assignee: Covidien LP, Mansfield, MA (US)

( * ) Notice: Subject to any disclaimer, the term of this patent is extended or adjusted under 35 U.S.C. 154(b) by 168 days.

This patent is subject to a terminal disclaimer.

(21) Appl. No.: 17/860,160

(22) Filed: Jul. 8, 2022

(65) Prior Publication Data

US 2022/0338916 A1 Oct. 27, 2022

Related U.S. Application Data

(63) Continuation of application No. 16/636,247, filed as application No. PCT/US2018/046619 on Aug. 14, 2018, now Pat. No. 11,406,441.

(Continued)

(51) Int. Cl.
*A61B 18/14* (2006.01)
*A61B 18/12* (2006.01)
(Continued)

(52) U.S. Cl.
CPC .......... *A61B 18/14* (2013.01); *A61B 18/1206* (2013.01); *A61B 34/37* (2016.02);
(Continued)

(58) Field of Classification Search
CPC . A61B 18/1206; A61B 18/14; A61B 18/1402; A61B 2017/00477;
(Continued)

(56) References Cited

U.S. PATENT DOCUMENTS 5,797,900 A * 8/1998 Madhani ................ A61B 34/30
606/1
6,132,368 A 10/2000 Cooper
(Continued)

FOREIGN PATENT DOCUMENTS

| CN | 106132322 A | 11/2016 |
|---|---|---|
| WO | 2016209769 A1 | 12/2016 |
| WO | 2017098279 A1 | 6/2017 |

OTHER PUBLICATIONS

Extended European Search Report issued in corresponding application EP 18845829.3 dated Apr. 9, 2021 (9 pages).

(Continued)

*Primary Examiner* — Michael F Peffley
(74) *Attorney, Agent, or Firm* — Carter, DeLuca & Farrell LLP

(57) ABSTRACT

An end effector is provided for use and connection to a robot arm of a robotic surgical system including a proximal hub, a distal hub, and a support hub. The distal hub is coupled to two opposing upright supports of the proximal hub about a first pivot axis. The support hub is coupled to two opposing upright supports of the distal hub about a second pivot axis. First and second drive members are coupled to opposing sides of the support hub and a third drive member is coupled to the distal hub. Simultaneous proximal translation of the first drive member and the second drive member causes the distal hub to pivot about the first pivot axis and proximal translation of only one of the first drive member or the second drive member causes the support hub to pivot about the second pivot axis.

18 Claims, 17 Drawing Sheets

Related U.S. Application Data

(60) Provisional application No. 62/546,066, filed on Aug. 16, 2017.

(51) Int. Cl.
*A61B 34/00* (2016.01)
*A61B 34/37* (2016.01)
*A61B 18/00* (2006.01)

(52) U.S. Cl.
CPC .... *A61B 34/71* (2016.02); *A61B 2018/00208* (2013.01); *A61B 2018/1253* (2013.01)

(58) Field of Classification Search
CPC .. A61B 2018/00208; A61B 2018/1253; A61B 2034/305; A61B 2034/715; A61B 34/30; A61B 34/37; A61B 34/71
See application file for complete search history.

(56) References Cited

U.S. PATENT DOCUMENTS

| | | | |
|---|---|---|---|
| 6,206,903 B1 | 3/2001 | Ramans | |
| 6,246,200 B1 | 6/2001 | Blumenkranz et al. | |
| 6,312,435 B1 | 11/2001 | Wallace et al. | |
| 6,331,181 B1 | 12/2001 | Tierney et al. | |
| 6,394,998 B1 * | 5/2002 | Wallace | A61B 34/35 901/29 |
| 6,424,885 B1 | 7/2002 | Niemeyer et al. | |
| 6,441,577 B2 | 8/2002 | Blumenkranz et al. | |
| 6,459,926 B1 | 10/2002 | Nowlin et al. | |
| 6,491,691 B1 | 12/2002 | Morley et al. | |
| 6,491,701 B2 | 12/2002 | Tierney et al. | |
| 6,493,608 B1 | 12/2002 | Niemeyer | |
| 6,554,844 B2 * | 4/2003 | Lee | A61B 5/0084 606/1 |
| 6,565,554 B1 | 5/2003 | Niemeyer | |
| 6,645,196 B1 | 11/2003 | Nixon et al. | |
| 6,659,939 B2 | 12/2003 | Moll | |
| 6,671,581 B2 | 12/2003 | Niemeyer et al. | |
| 6,676,684 B1 | 1/2004 | Morley et al. | |
| 6,685,698 B2 | 2/2004 | Morley et al. | |
| 6,699,235 B2 | 3/2004 | Wallace et al. | |
| 6,714,839 B2 | 3/2004 | Salisbury, Jr. et al. | |
| 6,716,233 B1 | 4/2004 | Whitman | |
| 6,728,599 B2 | 4/2004 | Wang et al. | |
| 6,746,443 B1 | 6/2004 | Morley et al. | |
| 6,766,204 B2 | 7/2004 | Niemeyer et al. | |
| 6,770,081 B1 | 8/2004 | Cooper et al. | |
| 6,772,053 B2 | 8/2004 | Niemeyer | |
| 6,783,524 B2 | 8/2004 | Anderson et al. | |
| 6,793,652 B1 | 9/2004 | Whitman et al. | |
| 6,793,653 B2 | 9/2004 | Sanchez et al. | |
| 6,799,065 B1 | 9/2004 | Niemeyer | |
| 6,837,883 B2 | 1/2005 | Moll et al. | |
| 6,839,612 B2 | 1/2005 | Sanchez et al. | |
| 6,840,938 B1 * | 1/2005 | Morley | A61B 34/71 901/29 |
| 6,843,403 B2 | 1/2005 | Whitman | |
| 6,846,309 B2 | 1/2005 | Whitman et al. | |
| 6,866,671 B2 | 3/2005 | Tierney et al. | |
| 6,871,117 B2 | 3/2005 | Wang et al. | |
| 6,879,880 B2 | 4/2005 | Nowlin et al. | |
| 6,899,705 B2 | 5/2005 | Niemeyer | |
| 6,902,560 B1 | 6/2005 | Morley et al. | |
| 6,936,042 B2 | 8/2005 | Wallace et al. | |
| 6,951,535 B2 | 10/2005 | Ghodoussi et al. | |
| 6,969,385 B2 * | 11/2005 | Moreyra | A61B 34/71 901/29 |
| 6,974,449 B2 | 12/2005 | Niemeyer | |
| 6,991,627 B2 | 1/2006 | Madhani et al. | |
| 6,994,708 B2 | 2/2006 | Manzo | |
| 7,048,745 B2 | 5/2006 | Tierney et al. | |
| 7,066,926 B2 | 6/2006 | Wallace et al. | |
| 7,101,363 B2 * | 9/2006 | Nishizawa | A61B 34/71 606/1 |
| 7,118,582 B1 | 10/2006 | Wang et al. | |
| 7,125,403 B2 | 10/2006 | Julian et al. | |
| 7,155,315 B2 | 12/2006 | Niemeyer et al. | |
| 7,239,940 B2 | 7/2007 | Wang et al. | |
| 7,306,597 B2 | 12/2007 | Manzo | |
| 7,357,774 B2 | 4/2008 | Cooper | |
| 7,373,219 B2 | 5/2008 | Nowlin et al. | |
| 7,379,790 B2 | 5/2008 | Toth et al. | |
| 7,386,365 B2 | 6/2008 | Nixon | |
| 7,391,173 B2 | 6/2008 | Schena | |
| 7,398,707 B2 | 7/2008 | Morley et al. | |
| 7,413,565 B2 | 8/2008 | Wang et al. | |
| 7,453,227 B2 | 11/2008 | Prisco et al. | |
| 7,524,320 B2 | 4/2009 | Tierney et al. | |
| 7,574,250 B2 | 8/2009 | Niemeyer | |
| 7,594,912 B2 | 9/2009 | Cooper et al. | |
| 7,607,440 B2 | 10/2009 | Coste-Maniere et al. | |
| 7,666,191 B2 | 2/2010 | Orban, III et al. | |
| 7,682,357 B2 | 3/2010 | Ghodoussi et al. | |
| 7,689,320 B2 | 3/2010 | Prisco et al. | |
| 7,695,481 B2 | 4/2010 | Wang et al. | |
| 7,695,485 B2 | 4/2010 | Whitman et al. | |
| 7,699,855 B2 | 4/2010 | Anderson et al. | |
| 7,713,263 B2 | 5/2010 | Niemeyer | |
| 7,725,214 B2 | 5/2010 | Diolaiti | |
| 7,727,244 B2 | 6/2010 | Orban, III et al. | |
| 7,741,802 B2 | 6/2010 | Prisco | |
| 7,756,036 B2 | 7/2010 | Druke et al. | |
| 7,757,028 B2 | 7/2010 | Druke et al. | |
| 7,762,825 B2 | 7/2010 | Burbank et al. | |
| 7,778,733 B2 | 8/2010 | Nowlin et al. | |
| 7,803,151 B2 | 9/2010 | Whitman | |
| 7,806,891 B2 | 10/2010 | Nowlin et al. | |
| 7,819,859 B2 | 10/2010 | Prisco et al. | |
| 7,819,885 B2 | 10/2010 | Cooper | |
| 7,824,401 B2 | 11/2010 | Manzo et al. | |
| 7,835,823 B2 | 11/2010 | Sillman et al. | |
| 7,843,158 B2 | 11/2010 | Prisco | |
| 7,865,266 B2 | 1/2011 | Moll et al. | |
| 7,865,269 B2 | 1/2011 | Prisco et al. | |
| 7,886,743 B2 | 2/2011 | Cooper et al. | |
| 7,899,578 B2 | 3/2011 | Prisco et al. | |
| 7,907,166 B2 | 3/2011 | Lamprecht et al. | |
| 7,935,130 B2 | 5/2011 | Williams | |
| 7,963,913 B2 | 6/2011 | Devengenzo et al. | |
| 7,983,793 B2 | 7/2011 | Toth et al. | |
| 8,002,767 B2 | 8/2011 | Sanchez | |
| 8,004,229 B2 | 8/2011 | Nowlin et al. | |
| 8,012,170 B2 | 9/2011 | Whitman et al. | |
| 8,054,752 B2 | 11/2011 | Druke et al. | |
| 8,062,288 B2 | 11/2011 | Cooper et al. | |
| 8,079,950 B2 | 12/2011 | Stern et al. | |
| 8,100,133 B2 | 1/2012 | Mintz et al. | |
| 8,108,072 B2 | 1/2012 | Zhao et al. | |
| 8,120,301 B2 | 2/2012 | Goldberg et al. | |
| 8,142,447 B2 | 3/2012 | Cooper et al. | |
| 8,147,503 B2 | 4/2012 | Zhao et al. | |
| 8,151,661 B2 | 4/2012 | Schena et al. | |
| 8,155,479 B2 | 4/2012 | Hoffman et al. | |
| 8,182,469 B2 | 5/2012 | Anderson et al. | |
| 8,202,278 B2 | 6/2012 | Orban, III et al. | |
| 8,206,406 B2 | 6/2012 | Orban, III | |
| 8,210,413 B2 | 7/2012 | Whitman et al. | |
| 8,216,250 B2 | 7/2012 | Orban, III et al. | |
| 8,220,468 B2 | 7/2012 | Cooper et al. | |
| 8,256,319 B2 | 9/2012 | Cooper et al. | |
| 8,285,517 B2 | 10/2012 | Sillman et al. | |
| 8,315,720 B2 | 11/2012 | Mohr et al. | |
| 8,335,590 B2 | 12/2012 | Costa et al. | |
| 8,347,757 B2 | 1/2013 | Duval | |
| 8,374,723 B2 | 2/2013 | Zhao et al. | |
| 8,418,073 B2 | 4/2013 | Mohr et al. | |
| 8,419,717 B2 | 4/2013 | Diolaiti et al. | |
| 8,423,182 B2 | 4/2013 | Robinson et al. | |
| 8,452,447 B2 | 5/2013 | Nixon | |
| 8,454,585 B2 | 6/2013 | Whitman | |
| 8,499,992 B2 | 8/2013 | Whitman et al. | |
| 8,508,173 B2 | 8/2013 | Goldberg et al. | |
| 8,528,440 B2 | 9/2013 | Morley et al. | |

(56) References Cited

U.S. PATENT DOCUMENTS

| | | |
|---|---|---|
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart |
| 8,989,903 B2 | 3/2015 | Weir et al. |
| 9,002,518 B2 | 4/2015 | Manzo |
| 9,014,856 B2 | 4/2015 | Manzo et al. |
| 9,016,540 B2 | 4/2015 | Whitman et al. |
| 9,019,345 B2 | 4/2015 | O'Grady et al. |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Arkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,295,522 B2 | 3/2016 | Kostrzewski |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,492,233 B2 | 11/2016 | Williams |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,675,354 B2 | 6/2017 | Weir et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |

(56) References Cited

U.S. PATENT DOCUMENTS

| | | |
|---|---|---|
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 10,939,969 B2 | 3/2021 | Swarup et al. |
| 10,939,973 B2 | 3/2021 | DiMaio et al. |
| 10,952,801 B2 | 3/2021 | Miller et al. |
| 10,965,933 B2 | 3/2021 | Jarc |
| 10,966,742 B2 | 4/2021 | Rosa et al. |
| 10,973,517 B2 | 4/2021 | Wixey |
| 10,973,519 B2 | 4/2021 | Weir et al. |
| 10,984,567 B2 | 4/2021 | Itkowitz et al. |
| 10,993,773 B2 | 5/2021 | Cooper et al. |
| 10,993,775 B2 | 5/2021 | Cooper et al. |
| 11,000,331 B2 | 5/2021 | Krom et al. |
| 11,013,567 B2 | 5/2021 | Wu et al. |
| 11,020,138 B2 | 6/2021 | Ragosta |
| 11,020,191 B2 | 6/2021 | Diolaiti et al. |
| 11,020,193 B2 | 6/2021 | Wixey et al. |
| 11,026,755 B2 | 6/2021 | Weir et al. |
| 11,026,759 B2 | 6/2021 | Donlon et al. |
| 11,040,189 B2 | 6/2021 | Vaders et al. |
| 11,045,077 B2 | 6/2021 | Stern et al. |
| 11,045,274 B2 | 6/2021 | Dachs, II et al. |
| 11,058,501 B2 | 7/2021 | Tokarchuk et al. |
| 11,076,925 B2 | 8/2021 | DiMaio et al. |
| 11,090,119 B2 | 8/2021 | Burbank |
| 11,096,687 B2 | 8/2021 | Flanagan et al. |
| 11,098,803 B2 | 8/2021 | Duque et al. |
| 11,109,925 B2 | 9/2021 | Cooper et al. |
| 11,116,578 B2 | 9/2021 | Hoffman et al. |
| 11,129,683 B2 | 9/2021 | Steger et al. |
| 11,135,029 B2 | 10/2021 | Suresh et al. |
| 11,147,552 B2 | 10/2021 | Burbank et al. |
| 11,147,640 B2 | 10/2021 | Jarc et al. |
| 11,154,373 B2 | 10/2021 | Abbott et al. |
| 11,154,374 B2 | 10/2021 | Hanuschik et al. |
| 11,160,622 B2 | 11/2021 | Goldberg et al. |
| 11,160,625 B2 | 11/2021 | Wixey et al. |
| 11,161,243 B2 | 11/2021 | Rabindran et al. |
| 11,166,758 B2 | 11/2021 | Mohr et al. |
| 11,166,770 B2 | 11/2021 | DiMaio et al. |
| 11,166,773 B2 | 11/2021 | Ragosta et al. |
| 11,173,597 B2 | 11/2021 | Rabindran et al. |
| 11,185,378 B2 | 11/2021 | Weir et al. |
| 11,191,596 B2 | 12/2021 | Thompson et al. |
| 11,197,729 B2 | 12/2021 | Thompson et al. |
| 11,213,360 B2 | 1/2022 | Hourtash et al. |
| 11,221,863 B2 | 1/2022 | Azizian et al. |
| 11,234,700 B2 | 2/2022 | Ragosta et al. |
| 11,241,274 B2 | 2/2022 | Vaders et al. |
| 11,241,290 B2 | 2/2022 | Waterbury et al. |
| 11,259,870 B2 | 3/2022 | DiMaio et al. |
| 11,259,884 B2 | 3/2022 | Burbank |
| 11,272,993 B2 | 3/2022 | Gomez et al. |
| 11,272,994 B2 | 3/2022 | Saraliev et al. |
| 11,291,442 B2 | 4/2022 | Wixey et al. |
| 11,291,513 B2 | 4/2022 | Manzo et al. |
| 11,406,441 B2 | 8/2022 | Traina |
| 2006/0079884 A1 | 4/2006 | Manzo |
| 2016/0303743 A1 | 10/2016 | Rockrohr |
| 2019/0099227 A1 | 4/2019 | Rockrohr |

OTHER PUBLICATIONS

International Search Report issued in corresponding Appl. No. PCT/US2018/046619 dated Dec. 11, 2018 (8 pages).

Office Action issued in corresponding Chinese Application No. 201880053171.7 issued Aug. 24, 2022, together with English language translation (21 pages).

* cited by examiner

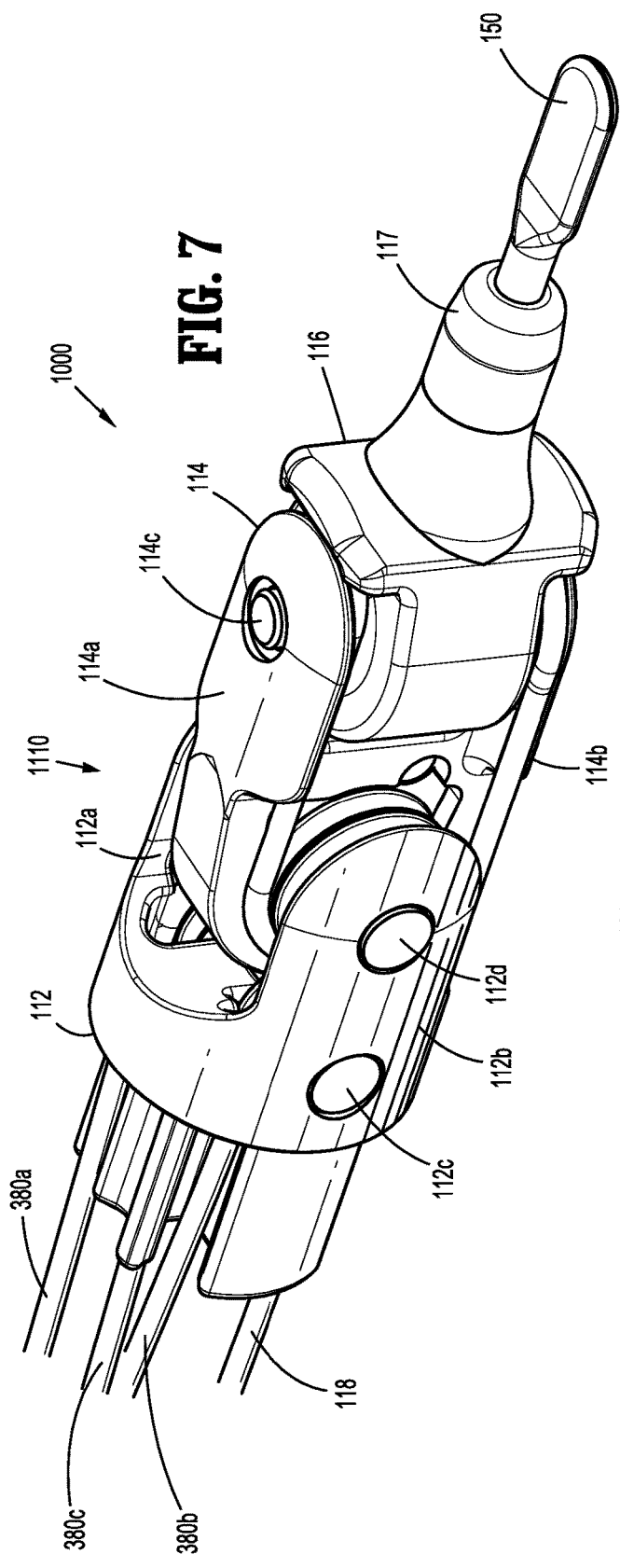
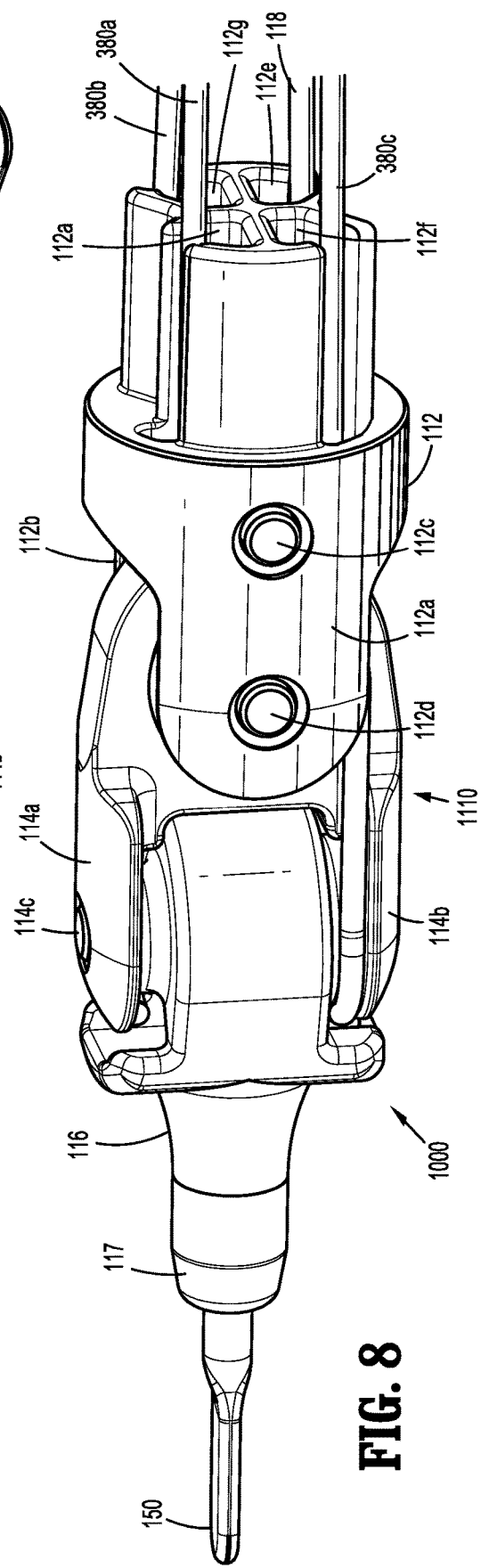

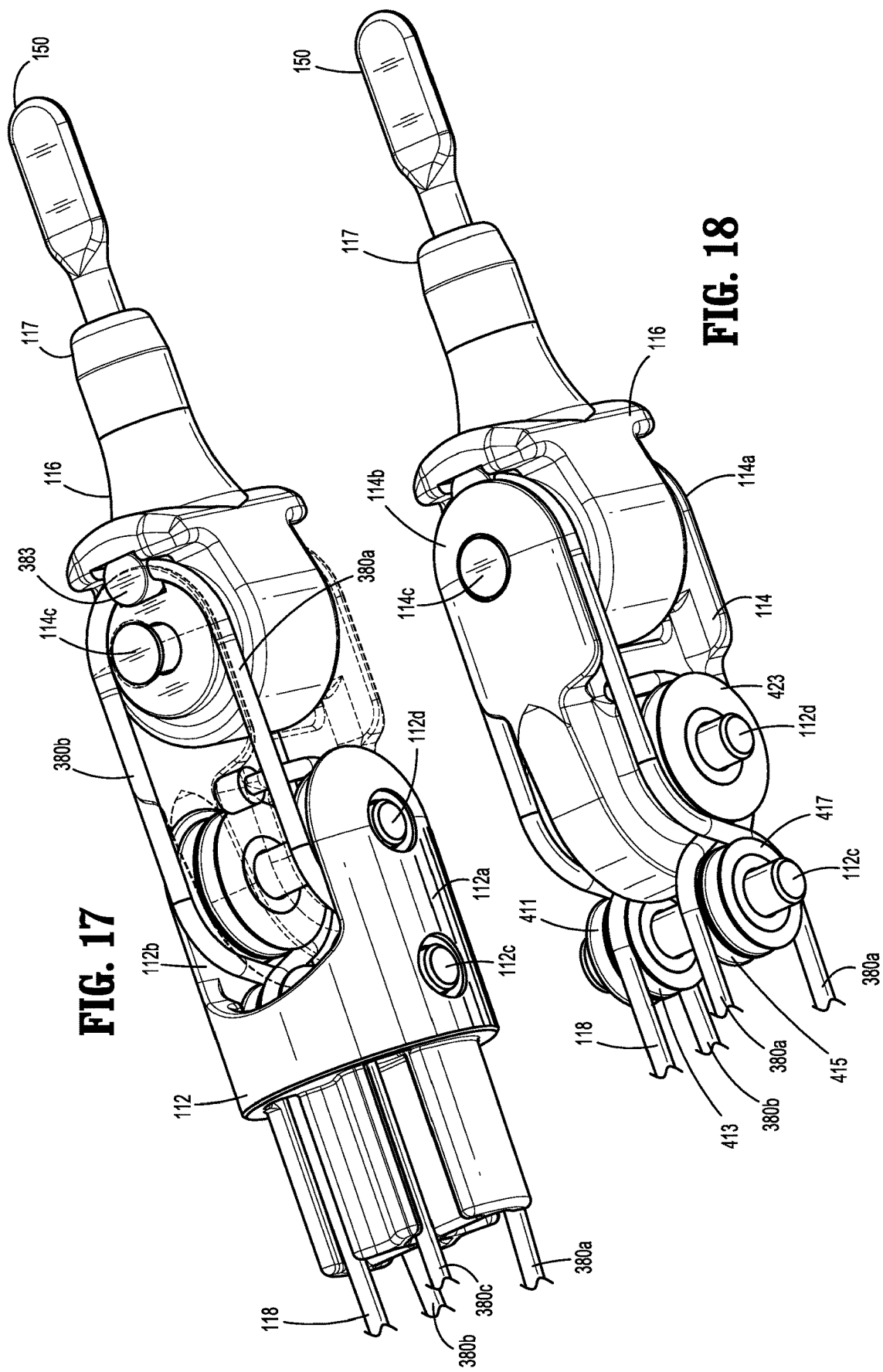

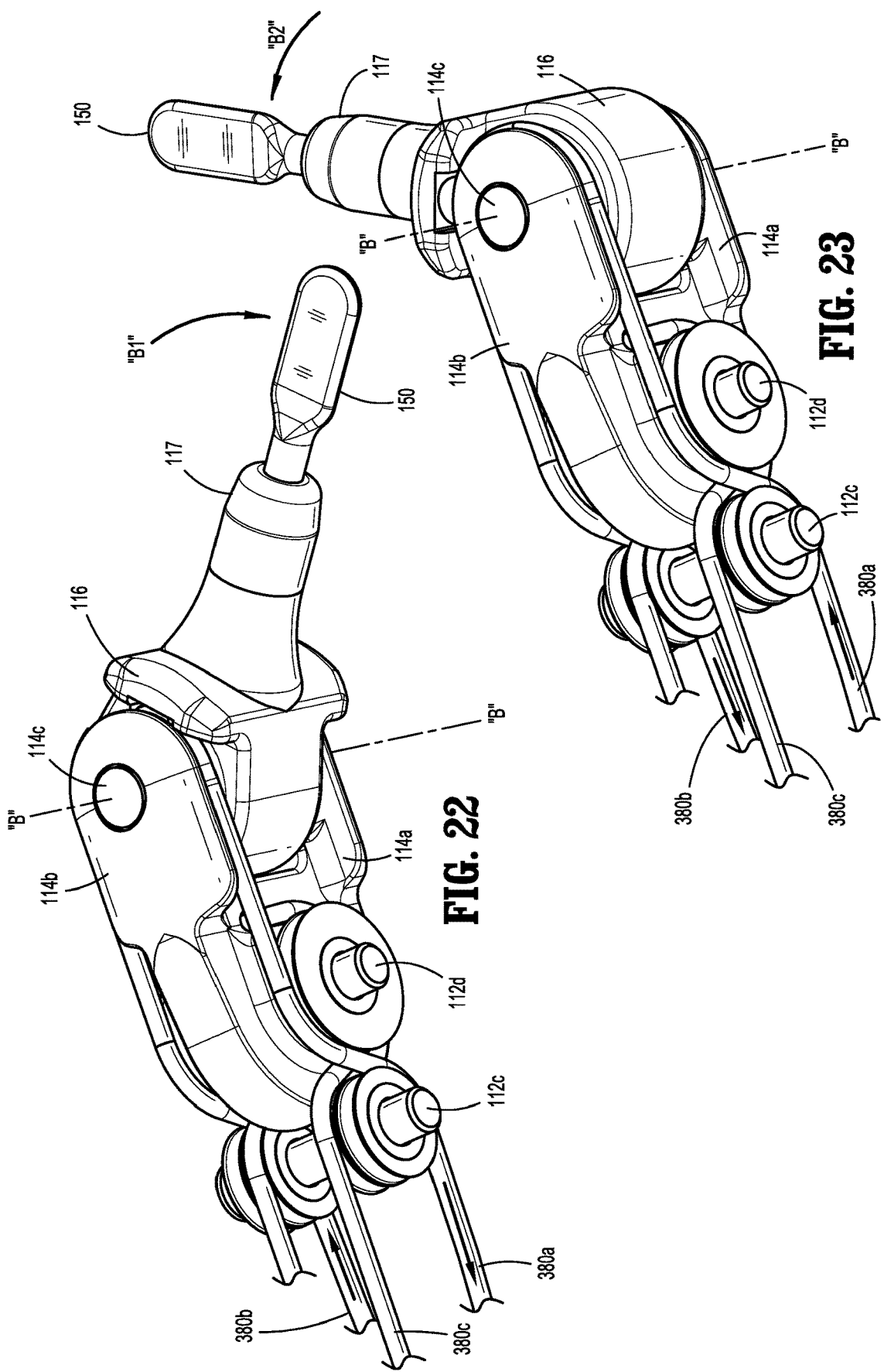

END EFFECTOR INCLUDING WRIST ASSEMBLY AND ELECTROSURGICAL TOOL FOR ROBOTIC SURGICAL SYSTEMS

CROSS-REFERENCE TO RELATED APPLICATIONS

This application is a continuation application of U.S. application Ser. No. 16/636,247, filed on Feb. 3, 2020, which is a National Stage Application of PCT Application Serial No. PCT/US2018/046619 under 35 U.S.C. § 371 (a), filed on Aug. 14, 2018, which claims the benefit of and priority to U.S. Provisional Patent Application Serial No. 62/546,066, filed on Aug. 16, 2017, the disclosures of each of the above-identified applications are hereby incorporated by reference in their entirety.

BACKGROUND

Robotic surgical systems have been used in minimally invasive medical procedures. Some robotic surgical systems include a console supporting a surgical robotic arm and a surgical instrument, having at least one end effector (e.g., forceps or a grasping tool), mounted to the robotic arm. The robotic arm provides mechanical power to the surgical instrument for its operation and movement. Each robotic arm may include an instrument drive unit that is operatively connected to the surgical instrument.

Cables extended from the robot console, through the robot arm, and connected to the wrist assembly and/or end effector. In some instances, the cables were actuated by means of motors that were controlled by a processing system including a user interface for a surgeon or clinician to be able to control the robotic surgical system including the robot arm, the wrist assembly and/or the end effector.

In some instances, the wrist assembly provided for articulation of the end effector through the use of four cables coupled to different components of the end effector or two cables used in combination with a pulley system coupled to components of the end effector. Each cable would be controlled by at least one motor. In such configurations, space within the components of the end effector was consumed by cables and space within the robotic arm was consumed by motors. Even more space-consuming were electrical cables traveling from the robotic arm to portions of the end effector.

As demand for smaller surgical tools with greater maneuverability and greater surgical capabilities increases, a need exists for end effectors that can be used with powered electrosurgical instruments. Additionally, a need exists for end effectors with articulation mechanisms that require fewer cables, motors, and components, thereby minimizing the cross sectional area of these tools, costs of the final products, cost of assembly, and the like.

SUMMARY

In accordance with an aspect of the present disclosure, an end effector for use with a robotic surgical system is provided. The end effector includes a proximal hub, a distal hub, and a support hub. The distal hub is coupled to two opposing upright supports of the proximal hub about a first pivot axis. The support hub is coupled to two opposing upright supports of the distal hub about a second pivot axis transverse to the first pivot axis. First and second drive members are coupled to opposing sides of the support hub and a third drive member is coupled to the distal hub.

In one aspect of the present disclosure, simultaneous proximal translation of the first drive member and the second drive member causes the distal hub to pivot about the first pivot axis. In some embodiments, proximal translation of only one of the first drive member or the second drive member causes the support hub to pivot about the second pivot axis.

Additionally, simultaneous proximal translation of the first drive member and the second drive member causes the distal hub to pivot about the first pivot axis in a first direction and proximal translation of the third drive member causes the distal hub to pivot about the first pivot axis in a second direction opposite the first direction. Additionally, proximal translation of the first drive member and distal translation of the second drive member may cause the support hub to pivot about the second pivot axis in a first direction and distal translation of the first drive member and proximal translation of the second drive member may cause the support hub to pivot about the second pivot axis in a second direction opposite the first direction.

The support hub may be configured to receive a monopolar tool. For example, the support hub may have an opening for receiving a monopolar tool therein. Additionally, the end effector may include a monopolar tool. The monopolar tool may be configured to couple to an electrosurgical generator via a power cable.

The end effector may further include a pulley system. The pulley system may include a first pulley, a second pulley, a third pulley, and a fourth pulley. Each of the first pulley, second pulley, third pulley, and fourth pulley can be operably coupled to the proximal hub via a proximal pulley pin and rotatable along the first pivot axis. The first drive member may wrap around at least a portion of the first pulley, the second drive member may wrap around at least a portion of the second pulley, the third drive member may wrap around at least a portion of the third pulley, and the power cable may wrap around at least a portion of the fourth pulley.

Additionally, or alternatively, the pulley system of the end effector may also include a fifth pulley, a sixth pulley, and a seventh pulley. Each of the fifth pulley, the sixth pulley, and the seventh pulley may be operably coupled to the proximal hub via a distal pulley pin. The first drive member may wrap around at least a portion of the fifth pulley, the second drive member may wrap around at least a portion of the sixth pulley, and the power cable may wrap around at least a portion of the seventh pulley.

According to another aspect of the present disclosure, an electromechanical surgical instrument for use with a robotic surgical system is provided. The electromechanical surgical instrument may include a drive assembly on its proximal portion and an end effector on its distal portion. The drive assembly may include a first drive screw having a first threaded shaft portion and a first nut threadingly coupled thereto, a second drive screw having a second threaded shaft portion and a second nut threadingly coupled thereto, and a third drive screw having a third threaded shaft portion and a third nut threadingly coupled thereto. Each of the first, second, and third drive screws may couple to a respective motor for rotating the respective drive screw. The end effector may include a proximal hub, a distal hub, and a support hub. The distal hub is coupled to two opposing upright supports of the proximal hub about a first pivot axis. The support hub is coupled to two opposing upright supports of the distal hub about a second pivot axis transverse to the first pivot axis.

The electromechanical surgical instrument may further include a first drive member, a second drive member, and a third drive member coupling portions of the end effector to portions of the drive assembly. In one aspect of the present disclosure, a proximal portion of the first drive member is coupled to the first drive nut and a distal portion of the first drive member is coupled to the support hub. Additionally, a proximal portion of the second drive member is coupled to the second drive nut and a distal portion of the second drive member is coupled to the support hub. Additionally, a proximal portion of the third drive member is coupled to the third drive nut and a distal portion of the third drive member is coupled to the distal hub.

Simultaneous proximal translation of the first drive member and the second drive member may cause the distal hub to pivot about the first pivot axis. In some embodiments, proximal translation of only one of the first drive member or the second drive member causes the support hub to pivot about the second pivot axis.

In one aspect of the present disclosure, simultaneous proximal translation of the first drive member and the second drive member causes the distal hub to pivot about the first pivot axis in a first direction and proximal translation of the third drive member causes the distal hub to pivot about the first pivot axis in a second direction opposite the first direction. Additionally, proximal translation of the first drive member and distal translation of the second drive member may cause the support hub to pivot about the second pivot axis in a first direction and distal translation of the first drive member and proximal translation of the second drive member may cause the support hub to pivot about the second pivot axis in a second direction opposite the first direction.

The support hub may be configured to receive a monopolar tool. For example, the support hub may have an opening for receiving a monopolar tool therein. Additionally, the end effector may include a monopolar tool. The monopolar tool may be configured to couple to an electrosurgical generator via a power cable.

The end effector may further include a pulley system. The pulley system may include a first pulley, a second pulley, a third pulley, and a fourth pulley. Each of the first pulley, second pulley, third pulley, and fourth pulley can be operably coupled to the proximal hub via a proximal pulley pin and rotatable along the first pivot axis. The first drive member may wrap around at least a portion of the first pulley, the second drive member may wrap around at least a portion of the second pulley, the third drive member may wrap around at least a portion of the third pulley, and the power cable may wrap around at least a portion of the fourth pulley.

Additionally, or alternatively, the pulley system of the end effector may also include a fifth pulley, a sixth pulley, and a seventh pulley. Each of the fifth pulley, the sixth pulley, and the seventh pulley may be operably coupled to the proximal hub via a distal pulley pin. The first drive member may wrap around at least a portion of the fifth pulley, the second drive member may wrap around at least a portion of the sixth pulley, and the power cable may wrap around at least a portion of the seventh pulley.

According to another aspect of the present disclosure, a robotic electrosurgical system is provided and includes an electrosurgical generator and an electromechanical surgical instrument having a monopolar tool configured to electrically couple to the electrosurgical generator.

The electromechanical surgical instrument of the robotic surgical system may include a drive assembly on its proximal portion and an end effector on its distal portion. The drive assembly may include a first drive screw having a first threaded shaft portion and a first nut threadingly coupled thereto, a second drive screw having a second threaded shaft portion and a second nut threadingly coupled thereto, and a third drive screw having a third threaded shaft portion and a third nut threadingly coupled thereto. Each of the first, second, and third drive screws may couple to a respective motor for rotating the respective drive screw. The end effector may include a proximal hub, a distal hub, and a support hub. The distal hub is coupled to two opposing upright supports of the proximal hub about a first pivot axis. The support hub is coupled to two opposing upright supports of the distal hub about a second pivot axis transverse to the first pivot axis.

The electromechanical surgical instrument may further include a first drive member, a second drive member, and a third drive member coupling portions of the end effector to portions of the drive assembly. In one aspect of the present disclosure, a proximal portion of the first drive member is coupled to the first drive nut and a distal portion of the first drive member is coupled to the support hub. Additionally, a proximal portion of the second drive member is coupled to the second drive nut and a distal portion of the second drive member is coupled to the support hub. Additionally, a proximal portion of the third drive member is coupled to the third drive nut and a distal portion of the third drive member is coupled to the distal hub.

The robotic electrosurgical system may further include motors and a control device configured to control articulation of the end effector or portions thereof. For example, the control device may control respective motors coupled to respective drive members. The control device may be configured to coordinate control of a first motor with control of a second motor by actuating the first motor in a first direction when actuating the second motor in a second direction opposite the first direction. Additionally, the control device may configured to coordinate control of the first motor and the second motor with control of a third motor by actuating the first motor and the second motor in a first direction when actuating the third motor in a second direction opposite the first direction.

The control device may be configured to cause simultaneous proximal translation of the first drive member and the second drive member which causes the distal hub to pivot about the first pivot axis. In some embodiments, proximal translation of only one of the first drive member or the second drive member causes the support hub to pivot about the second pivot axis.

Additionally, the control device may be configured to cause simultaneous proximal translation of the first drive member and the second drive member which causes the distal hub to pivot about the first pivot axis in a first direction and to cause proximal translation of the third drive member which causes the distal hub to pivot about the first pivot axis in a second direction opposite the first direction. Additionally, proximal translation of the first drive member and distal translation of the second drive member may cause the support hub to pivot about the second pivot axis in a first direction and distal translation of the first drive member and proximal translation of the second drive member may cause the support hub to pivot about the second pivot axis in a second direction opposite the first direction.

The support hub may have an opening for receiving the monopolar tool therein. The monopolar tool may be configured to couple to the electrosurgical generator via a power cable.

The end effector may further include a pulley system. The pulley system may include a first pulley, a second pulley, a third pulley, and a fourth pulley. Each of the first pulley, second pulley, third pulley, and fourth pulley can be operably coupled to the proximal hub via a proximal pulley pin and rotatable along the first pivot axis. The first drive member may wrap around at least a portion of the first pulley, the second drive member may wrap around at least a portion of the second pulley, the third drive member may wrap around at least a portion of the third pulley, and the power cable may wrap around at least a portion of the fourth pulley.

Additionally, or alternatively, the pulley system of the end effector may also include a fifth pulley, a sixth pulley, and a seventh pulley. Each of the fifth pulley, the sixth pulley, and the seventh pulley may be operably coupled to the proximal hub via a distal pulley pin. The first drive member may wrap around at least a portion of the fifth pulley, the second drive member may wrap around at least a portion of the sixth pulley, and the power cable may wrap around at least a portion of the seventh pulley.

BRIEF DESCRIPTION OF THE DRAWINGS

Embodiments of the present disclosure are described herein with reference to the accompanying drawings, wherein:

FIG. 7 is a side, perspective view of the end effector of FIG. 6;

FIG. 8 is another side, perspective view of the end effector of FIG. 6;

FIG. 17 is a side, perspective view of the end effector of FIG. 6, with parts removed, and illustrating a pulley system thereof;

FIG. 18 is a side, perspective view of the end effector of FIG. 6, with parts removed, and illustrating the pulley system thereof;

FIG. 22 is a side, perspective view of the end effector of FIG. 6, with parts removed, illustrating the pulley system thereof and illustrating the wrist assembly thereof in a further articulated condition; and FIG. 23 is a side, perspective view of the end effector of FIG. 6, with parts removed, illustrating the pulley system thereof and illustrating the wrist assembly thereof in a further articulated condition.

DETAILED DESCRIPTION

Figure 1:
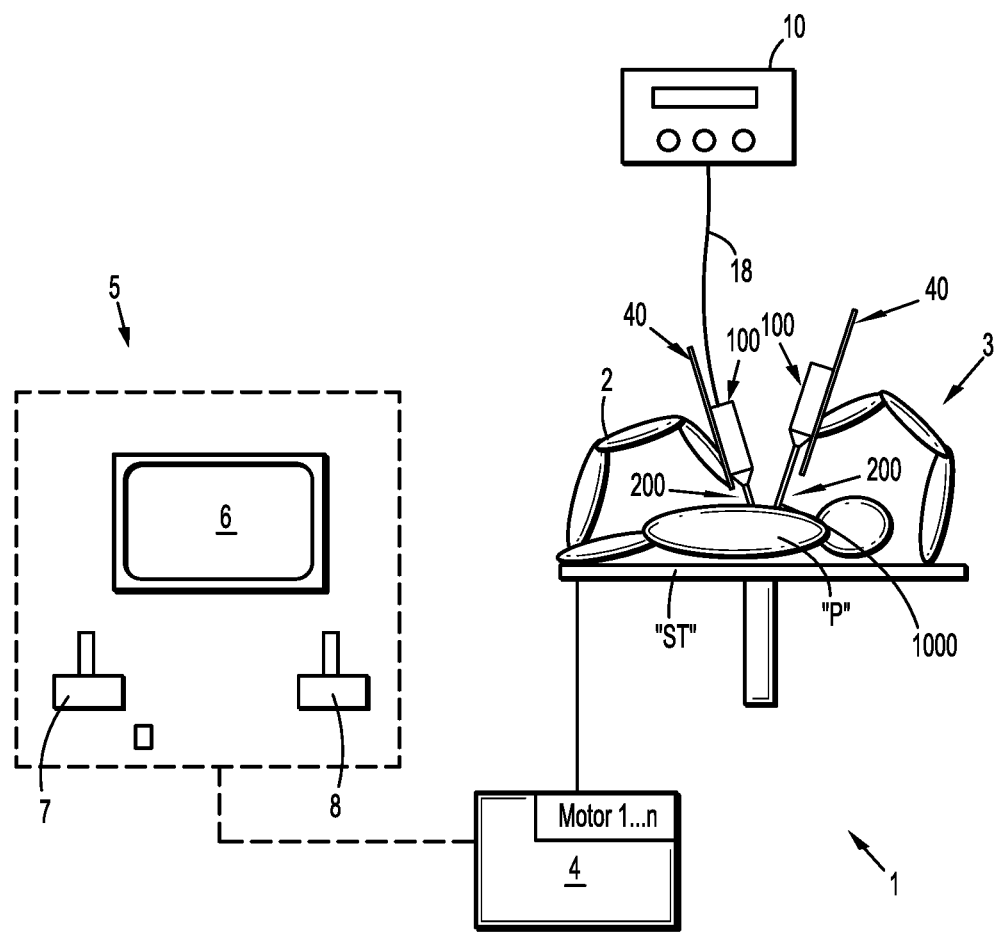
FIG. 1 is a schematic illustration of a robotic surgical system including a robotic surgical assembly in accordance with the present disclosure.

Embodiments of the presently disclosed surgical assembly including an instrument drive unit for driving the operation of an electromechanical surgical instrument and methods thereof are described in detail with reference to the drawings, in which like reference numerals designate identical or corresponding elements in each of the several views. As used herein, the term "distal" refers to that portion of the robotic surgical system, surgical assembly, or component thereof, that is closer to a patient, while the term "proximal" refers to that portion of the robotic surgical system, surgical assembly, or component thereof, that is further from the patient. As used herein, the terms parallel and perpendicular are understood to include relative configurations that are substantially parallel and substantially perpendicular up to about + or −10 degrees from true parallel and true perpendicular.

As used herein, the term "clinician" refers to a doctor, nurse, or other care provider and may include support personnel. In the following description, well-known functions or construction are not described in detail to avoid obscuring the present disclosure in unnecessary detail.

As will be described in detail below, provided is a surgical assembly configured to be attached to a surgical robotic arm. The surgical assembly includes an instrument drive unit having, for example, but not limited to, a motor configured to rotate an electromechanical instrument about a longitudinal axis thereof. In some embodiments, the motor may be a hollow core motor. Additionally, provided is a feedback assembly configured to determine and regulate the degree of rotation of the electromechanical instrument about its longitudinal axis. The rotation of the electromechanical instrument may be achieved with a hollow core motor, a canister motor (brushless or brushed), via a transmission (gear, belt and/or cable); via pneumatics, and/or via hydraulics. The axis of rotation of the electromechanical instrument may be integral to the instrument drive unit or to the robotic arm.

Referring initially to FIG. 1, a surgical system, such as, for example, a robotic surgical system 1, generally includes one or more surgical robotic arms 2, 3, a control device 4, and an operating console 5 coupled with control device 4. Any of the surgical robotic arms 2, 3 may have a robotic surgical assembly 100 and an electromechanical surgical instrument 200 coupled thereto. The electromechanical surgical instrument 200 includes an end effector 1000 disposed at a distal portion thereof. In some embodiments, the robotic surgical assembly 100 may be removably attached to a slide rail 40 of one of the surgical robotic arms 2, 3. In certain embodiments, the robotic surgical assembly 100 may be fixedly attached to the slide rail 40 of one of the surgical robotic arms 2, 3.

Operating console 5 includes a display device 6, which is set up to display three-dimensional images; and manual input devices 7, 8, by means of which a clinician (not shown), is able to telemanipulate the robotic arms 2, 3 in a first operating mode, as known in principle to a person skilled in the art. Each of the robotic arms 2, 3 may be composed of any number of members, which may be connected through joints. The robotic arms 2, 3 may be driven by electric drives (not shown) that are connected to control device 4. The control device 4 (e.g., a computer) is set up to activate the drives, for example, by means of a computer program, in such a way that the robotic arms 2, 3, the attached robotic surgical assembly 100, and thus the electromechanical surgical instrument 200 (including the end effector 1000) execute a desired movement according to a movement defined by means of the manual input devices 7, 8. The control device 4 may also be set up in such a way that it regulates the movement of the robotic arms 2, 3 and/or of the drives.

The robotic surgical system 1 is configured for use on a patient "P" positioned (e.g., lying) on a surgical table "ST" to be treated in a minimally invasive manner by means of a surgical instrument, e.g., the electromechanical surgical instrument 200 and more specifically the end effector 1000 of the electromechanical surgical instrument 200. The robotic surgical system 1 may also include more than two robotic arms 2, 3, the additional robotic arms likewise connected to the control device 4 and telemanipulatable by means of the operating console 5. A surgical instrument, for example, the electromechanical surgical instrument 200 (including the end effector 1000 thereof), may also be attached to any additional robotic arm(s).

The control device 4 may control one or more motors, e.g., motors (not shown), each motor configured to drive movement of the robotic arms 2, 3 in any number of directions. Further, the control device 4 may control an instrument drive unit 110 including motors 52a, 52b, and 52c of a motor pack 50 disposed within a sterile barrier housing 130 of the robotic surgical assembly 100. The motors 52a, 52b, and 52c of the motor pack 50 drive various operations of the end effector 1000 of the electromechanical surgical instrument 200. The motors 52a, 52b, and 52c may include a rotation motor, such as, for example, a canister motor. One or more of the motors 52a, 52b, and 52c (or a different motor, not shown) may be configured to drive a relative rotation of the electromechanical surgical instrument 200, or components thereof, along a longitudinal axis thereof. In some embodiments, each motor 52a, 52b, and 52c of motor pack 50 can be configured to actuate (e.g., rotate) respective drive screws 340a, 340b, 340c (FIG. 4) (or, for example, a linear drive, a capstan, etc.) which is operatively connected to a drive rod or a lever arm to effect operation and/or movement of the electromechanical end effector 1000 of the electromechanical surgical instrument 200.

With continued reference to FIG. 1, the robotic surgical system 1 includes the robotic surgical assembly 100 that is coupled with or to the robotic arm 2 or 3, and the electromechanical surgical instrument 200 that is coupled to the robotic surgical assembly 100. The robotic surgical assembly 100 transfers power and actuation forces from its motors to driven members of the electromechanical surgical instrument 200 to ultimately drive movement of components of the end effector 1000 of electromechanical surgical instrument 200, for example, an articulation/rotation/pitch/yaw of the end effector 1000. The robotic surgical assembly 100 may also be configured for the activation or firing of an electrosurgical energy-based instrument or the like (e.g., cable drives, pulleys, friction wheels, rack and pinion arrangements, etc.).

As described above, instrument drive unit 110 of robotic surgical assembly 100 includes motor pack 50 and sterile barrier housing 130. Motor pack 50 includes motors 52a, 52b, 52c for controlling various operations of end effector 1000 of electromechanical surgical instrument 200. Electromechanical surgical instrument 200 is removably coupleable to instrument drive unit 110 and instrument drive unit 110 is removably coupleable or fixedly coupled to slide rail 40 (FIG. 1) of one of the surgical robotic arms 2, 3.

As described in greater detail below, in use, as the motors 52a, 52b, 52c of the motor pack 50 are actuated, rotation of the drive shafts 54a, 54b, 54c of the motors 52a, 52b, 52c, respectively, is transferred to the respective proximal couplers 310a, 310b, 310c of the drive assemblies 300a, 300b, 300c (FIG. 3) of the electromechanical surgical instrument 200.

Figure 3:
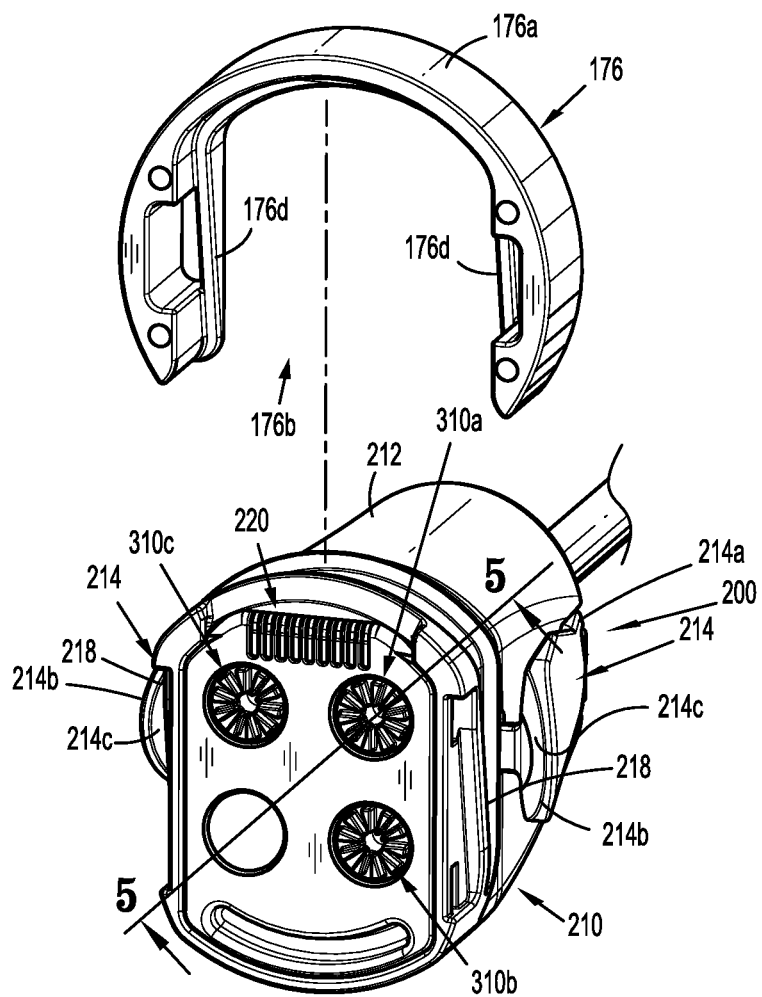
FIG. 3 is a rear perspective view of the electromechanical surgical instrument for use with the robotic surgical assembly of FIGS. 2A and 2B.
Figure 4:
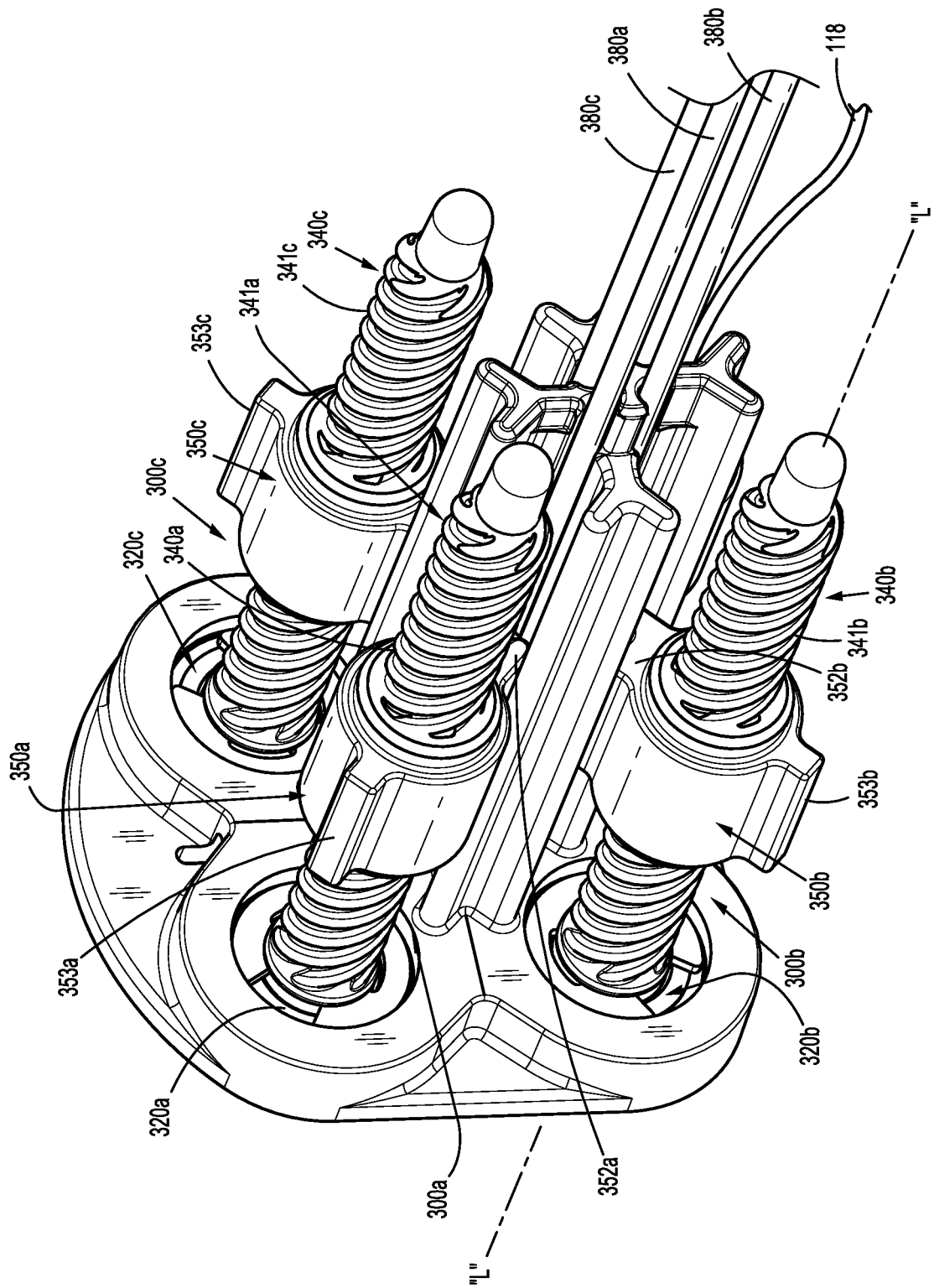
FIG. 4 is a perspective view of drive assemblies of the electromechanical surgical instrument of FIG. 3.
Figure 5:
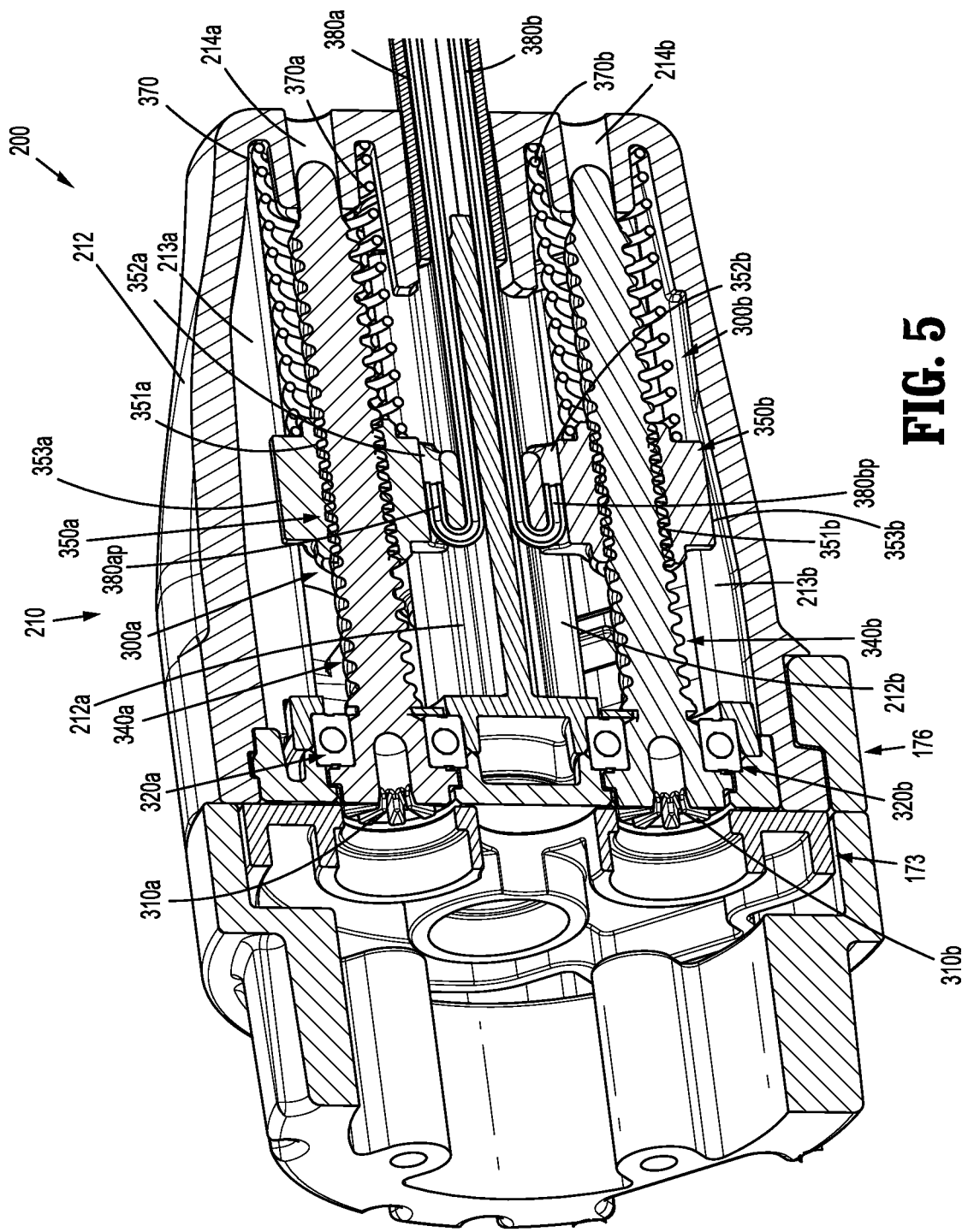
FIG. 5 is a cross-sectional view, as taken through 5-5 of FIG. 3.
Figure 6:
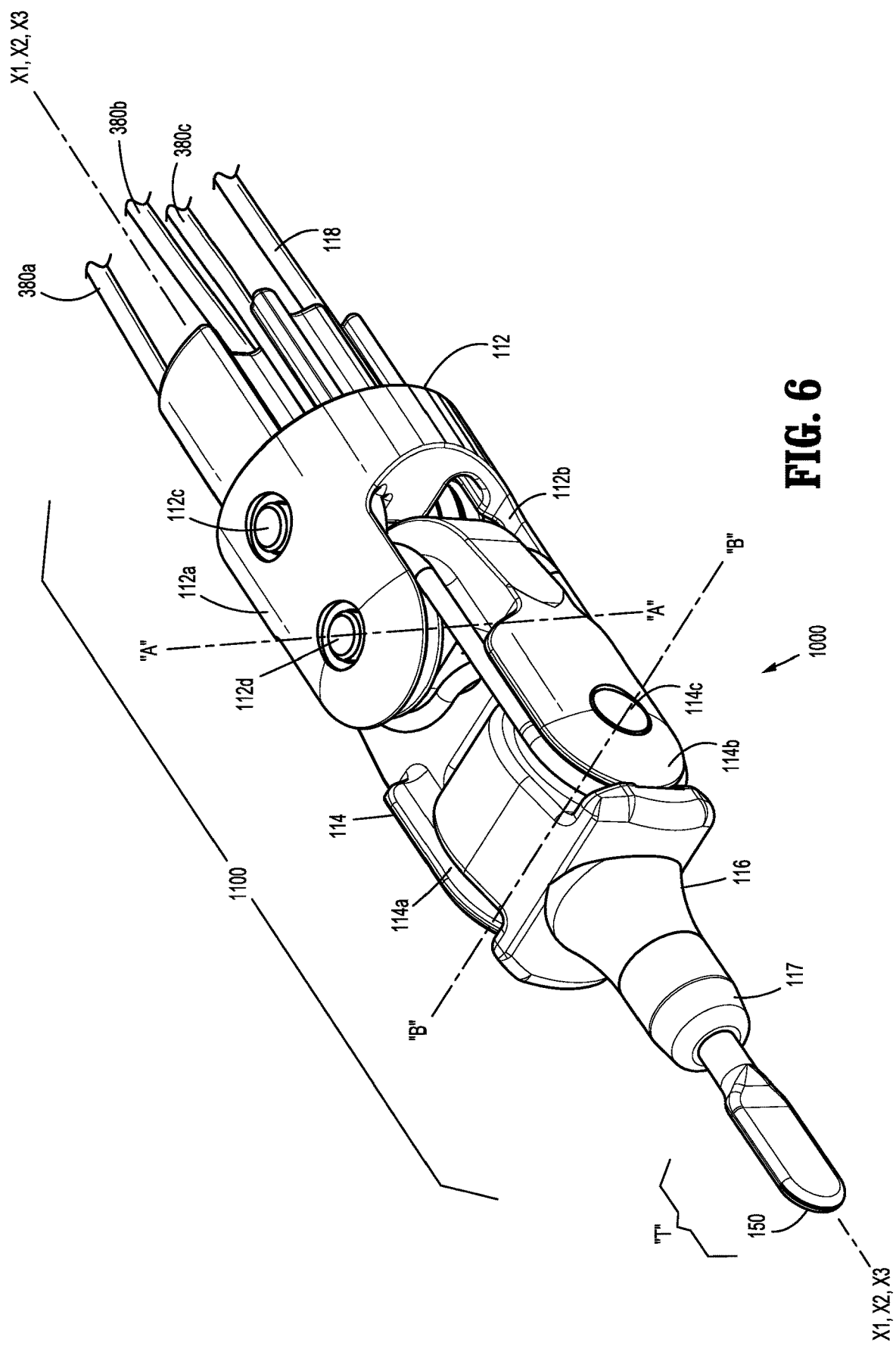
FIG. 6 is a top, perspective view of an end effector including a monopolar tool, according to an embodiment of the present disclosure, for use in the robotic surgical system of FIG. 1.
Figure 9:
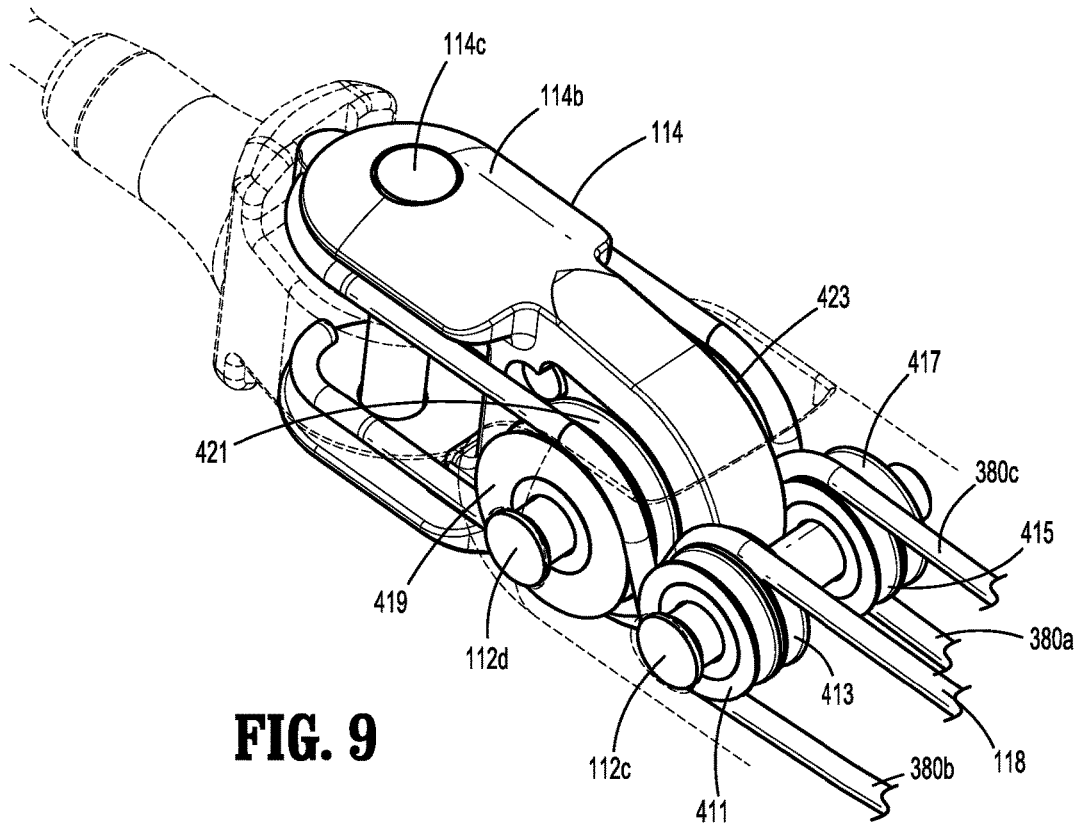
FIG. 9 is another side, perspective view of the end effector of FIG. 6, with parts removed.
Figure 10:
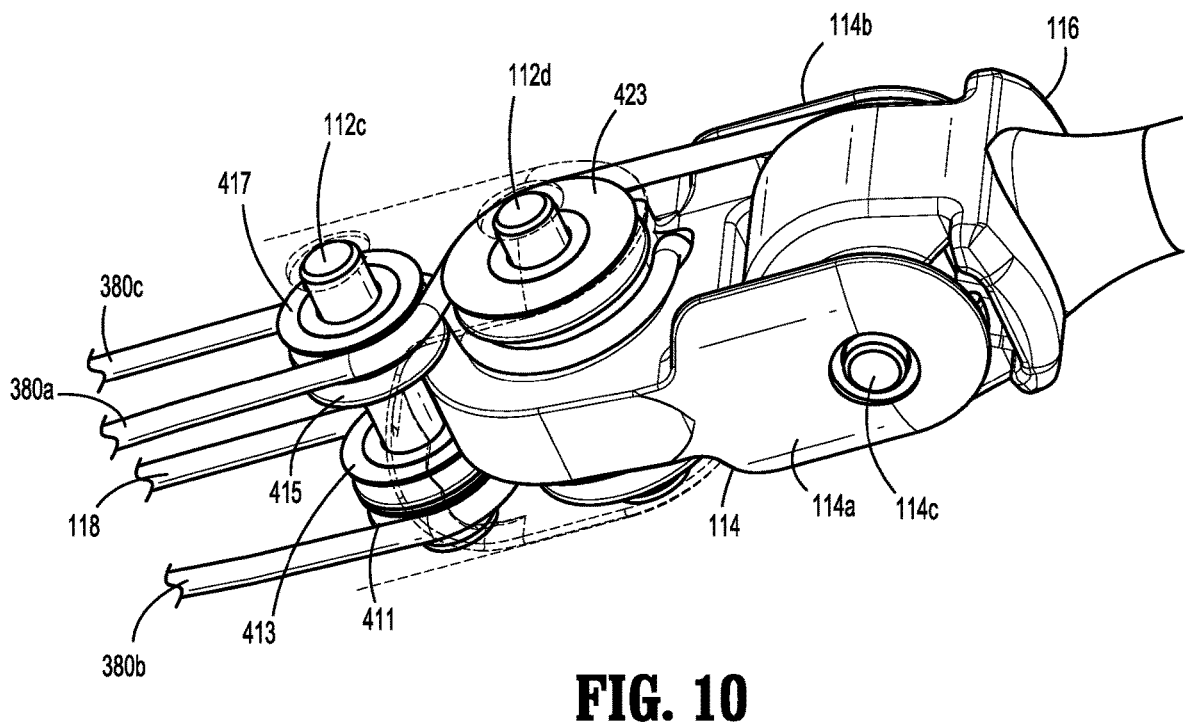
FIG. 10 is a bottom, perspective view of the end effector of FIG. 6, with parts removed.

Turning now to FIGS. 3-5, a proximal portion of the electromechanical surgical instrument 200 is shown and will be described. The electromechanical surgical instrument 200 may have a surgical instrument or end effector 1000 (FIGS. 6-23) secured to or securable to a distal end thereof. The electromechanical surgical instrument 200 is configured to transfer rotational forces/movement supplied by the robotic surgical assembly 100 (e.g., via the motors 52a, 52b, 52c of the motor pack 50) into longitudinal movement or translation of the drive members 380a, 380b, 380c to effect various functions of the end effector 1000.

The electromechanical surgical instrument 200 includes a housing assembly 210 including a housing 212 defining at least one cavity or bore 212a, 212b, 212c, 212d therein which is configured to receive a respective drive assembly 300a, 300b, 300c and a power cable 118 therein. In accordance with the present disclosure, each bore 212a, 212b, 212c of the housing 212 is configured to operatively support a respective drive assembly 300a, 300b, and 300c therein and the bore 212d is configured to operatively support a power cable 118 therein.

As illustrated in FIGS. 3-5, each bore 212a, 212b, 212c of the housing 212 defines a respective longitudinally extending groove or channel 213a, 213b, 213c therein. Each channel 213a, 213b, 213c is configured to slidingly accept a rail or tab 353a, 353b, 353c extending radially from a respective drive nut 350a, 350b, 350c of a respective drive assembly 300a, 300b, 300c, as will be described in greater detail below.

Figure 2A:
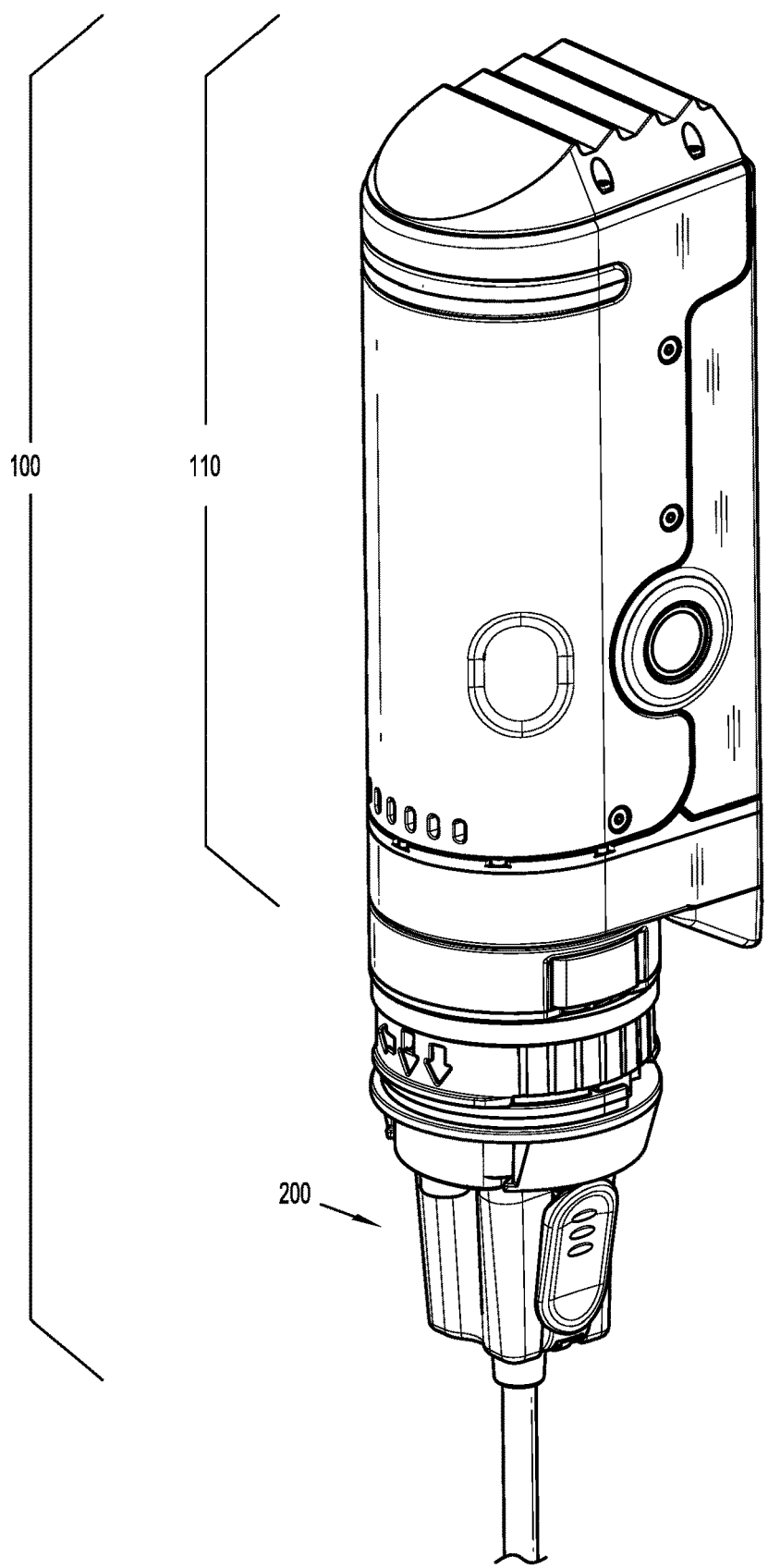
FIG. 2A is a perspective view of the robotic surgical assembly and the electromechanical surgical instrument, in accordance with an embodiment of the present disclosure.
Figure 2B:
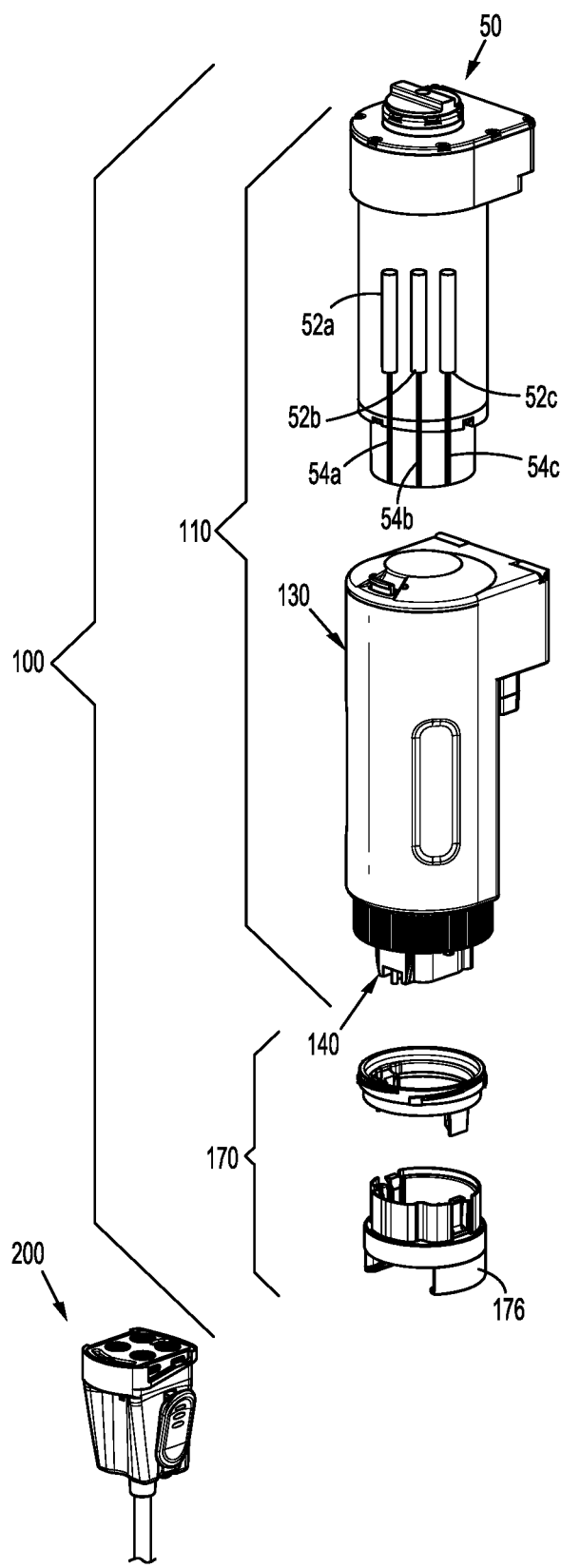
FIG. 2B is a perspective view, with parts separated, of the robotic surgical assembly and the electromechanical surgical instrument shown in FIG. 2A.

When the electromechanical surgical instrument 200 is fully connected to the robotic surgical assembly 100, the proximal couplers 310a, 310b, 310c of the drive assemblies 300a, 300b, 300c of the electromechanical surgical instrument 200 come into registration with and are connected to respective drive shafts 54a, 54b, 54c within the instrument drive unit 110 (FIGS. 2A and 2B) to couple the respective drive assemblies 300a, 300b, 300b to respective motors 52a, 52b, 52c of the robotic surgical assembly 100.

The housing 212 of the housing assembly 210 of the electromechanical surgical instrument 200 supports an electrical connector 220 (FIG. 3) configured for selective connection to the plug 140 of the instrument drive unit 110 (FIGS. 2A and 2B) of the robotic surgical assembly 100. The electromechanical surgical instrument 200 may include electronics, including, and not limited to, a memory (for storing identification information, usage information, and the like), wired or wireless communication circuitry (for receiving and transmitting data or information from/to the electromechanical surgical instrument 200, from/to control device 4, and/or from/to a remote central processing system). The robotic surgical assembly 100 may be configured to permit passage or routing of a dedicated electrocautery cable (for example, cable 118) or the like for use and connection to an electrosurgical based electromechanical surgical instrument (e.g., for ablation, coagulation, sealing, etc.). The electrical connector 220 may include and is not limited to conductive connectors, magnetic connectors, resistive connectors, capacitive connectors, Hall sensors, reed switches or the like.

With continued reference to FIGS. 3-5, the housing assembly 210 of the electromechanical surgical instrument 200 houses a plurality of drive assemblies, shown as drive assemblies 300a, 300b, 300c. In the illustrated embodiment, the electromechanical surgical instrument 200 includes three drive assemblies 300a, 300b, 300c; however, the electromechanical surgical instrument 200 may include more (e.g., four, five, or six) or fewer (e.g., two) drive assemblies without departing from the scope of the present disclosure.

Each drive assembly 300a, 300b, 300c includes a respective proximal coupler 310a, 310b, 310, proximal bearing 320a, 320b, 320c, drive screw 340a, 340b, 340c, drive nut 350a, 350b, 350c, biasing element 370a, 370b, 370c, and drive member (e.g., a drive rod or drive cable) 380a, 380b, 380c. The proximal coupler 310a, 310b, 310c of each drive assembly 300a, 300b, 300c is configured to meshingly engage with a respective drive couplers (not shown) coupled to respective motors of the robotic surgical assembly 100. In operation, rotation of the drive transfer shafts 54a, 54b, 54c of the motors 52a, 52b, 52c results in corresponding rotation of respective proximal coupler 310a, 310b, 310c of respective drive assembly 300a, 300b, 300c.

The proximal coupler 310a, 310b, 310c of each drive assembly 300a, 300b, 300c is keyed to or otherwise non-rotatably connected to a proximal end of a respective drive screw 340a, 340b, 340c. Accordingly, rotation of the proximal coupler 310a, 310b, 310c results in a corresponding rotation of a respective drive screw 340a, 340b, 340c.

Each proximal bearing 320a, 320b, 320c is disposed about a proximal portion of a respective drive screw 340a, 340b, 340c adjacent a proximal end of the housing 212 of the housing assembly 210. A distal end or tip of each drive screw 340a, 340b, 340c may be rotatably disposed or supported in a respective recess 214a, 214b, 214c defined in a distal end of the housing 212 (see FIG. 5).

Each of the drive screws 340a, 340b, 340c includes a threaded body or shaft portion 341a, 341b, 341c, and defines a longitudinal axis "L-L" extending through a radial center thereof (see FIG. 4). In use, rotation of the proximal coupler 310a, 310b, 310c, as described above, results in rotation of a respective drive screw 340a, 340b, 340c about longitudinal axis "L-L", in a corresponding direction and rate of rotation.

Each of the drive nuts 350a, 350b, 350c (or capstan) includes a threaded aperture 351a, 351b, 351c extending longitudinally therethrough, which is configured to mechanically engage the threaded shaft portion 341a, 341b, 341c of a respective drive screw 340a, 340b, 340c. Each drive nut 350a, 350b, 350c is configured to be positioned on a respective drive screw 340a, 340b, 340c in a manner such that rotation of the drive screw 340a, 340b, 340c causes longitudinal movement or translation of the respective drive nut 350a, 350b, 350c. Moreover, rotation of the proximal coupler 310a, 310b, 310c in a first direction (e.g., clockwise) causes the respective drive nut 350a, 350b, 350c to move in a first longitudinal direction (e.g., proximally) along the respective drive screw 340a, 340b, 340c, and rotation of the proximal coupler 310a, 310b, 310c in a second direction (e.g., counter-clockwise) causes the respective drive nut 350a, 350b, 350c to move in a second longitudinal direction (e.g., distally) with respect to the respective drive screw 340a, 340b, 340c.

Each drive nut 350a, 350b, 350c includes a retention pocket formed in an engagement tab 352a, 352b, 352c formed therein that is disposed adjacent the threaded aperture 351a, 351b, 351c thereof. Each retention pocket is configured to retain a proximal end 380ap, 380bp, 380cp of a respective drive member 380a, 380b, 380c, as discussed in further detail below.

Each drive nut 350a, 350c, 350c includes a tab 353a, 353b, 353c extending radially from and longitudinally along an outer surface thereof. The tab 353a, 353b, 353c of each drive nut 350a, 350b, 350c is configured to be slidably disposed in a respective longitudinally extending channel 213a, 213b, 213c formed in the bores 212a, 212b, 212c of the housing 212. The tab 353a, 353b, 353c of each drive nut 350a, 350b, 350c cooperates with a respective channel 213a, 213b, 213c of the bore 212a, 212b, 212c of the housing 212 to inhibit or prevent each drive nut 350a, 350b, 350c from rotating about longitudinal axis "L-L" as each drive screw 340a, 340b, 340c is rotated.

Each drive nut 350a, 350b, 350c includes an engagement portion 352a, 352b, 352c disposed adjacent a radially inward surface thereof, which is configured to mechanically engage or retain a proximal portion 380ap, 380bp, 380cp of a respective drive member 380a, 380b, 380c. In operation, as the drive nuts 350a, 350b, 350c are axially displaced along the drive screw 340a, 340b, 340c, the drive nuts 350a, 350b, 350c transmit concomitant axial translation to the drive member 380a, 380b, 380c.

A biasing element 370a, 370b, 370c, e.g., a compression spring, is configured to radially surround a respective distal portion of the threaded shaft portion 341a, 341b, 341c of each drive screw 340a, 340b, 340c. Each biasing element 370a, 370b, 370c is interposed between a respective drive nut 350a, 350b, 350c and a distal surface of the housing 212 of the housing assembly 210.

Each drive member 380a, 380b, 380c extends distally from a respective drive nut 350a, 350b, 350c, through a respective central bore or channel 212a, 212b, 212c of the housing 212 of the housing assembly 210, and is configured to mechanically engage a portion of a surgical instrument, e.g., a portion or component of end effector 1000, of the electromechanical surgical instrument 200 as will be described in greater detail below with reference to FIGS. 6-23. Additionally, power cable 118 extends distally through central bore or channel 212d of the housing 212 of the housing assembly 210, and is configured to electrically couple to a monopolar tool 150 of end effector 1000.

In operation, longitudinal translation of at least one drive member 380a, 380b, 380c is configured to drive a function of the end effector 1000 of the electromechanical surgical instrument 200. For example, a proximal translation of drive member 380c may be configured to articulate the end effector 1000 or a portion of the end effector 1000 in a first direction. It is envisioned that while drive member 380c is translated in a proximal direction, drive nuts 350a and 350b are translated in a distal direction to enable corresponding translation of respective drive members 380a and 380b in a distal direction, as will be described in greater detail below. Additionally, for example, a proximal translation of drive members 380a and 380b of the electromechanical surgical instrument 200 may be configured to articulate the end effector 1000, or a portion of the end effector 1000 in a second direction. It is envisioned that while drive members 380a and 380b are translated in a proximal direction, drive nut 350c is translated in a distal direction to enable corresponding translation of drive member 380c in a distal direction, as will be described in greater detail below.

In accordance with the present disclosure, a distal portion of at least one of the drive members 380a, 380b, 380c may include a flexible portion, while a proximal portion of the drive members 380a, 380b, 380c are rigid, such that the flexible distal portion may follow a particular path through the electromechanical surgical instrument 200. Accordingly, the biasing members 370a, 370b, 370c may function to maintain the drive members 380a, 380b, 380c in tension to prevent slack or to reduce the amount of slack in the flexible distal portion of the drive members 380a, 380b, 380c.

During use of the electromechanical surgical instrument 200 (e.g., when motor 52a, 52b, 52c of the robotic surgical assembly 100, or other powered drives, are used to rotate one or more of proximal couplers 310a, 310b, 310c), rotation of a proximal coupler 310a, 310b, 310c results in a corresponding rotation of the respective drive screw 340a, 340b, 340c. Rotation of the drive screw 340a, 340b, 340c causes longitudinal translation of the respective drive nut 350a, 350b, 350c due to the engagement between the threaded portion 341a, 341b, 341c of the drive screw 340a, 340b, 340c and the threaded aperture 351a, 351b, 351c of the drive nut 350a, 350b, 350c. As discussed above, the direction of longitudinal translation of the drive nut 350a, 350b, 350c is determined by the direction of rotation of the proximal coupler 310a, 310b, 310c, and thus, the respective drive screw 340a, 340b, 340c. For example, clockwise rotation of the drive screw 340a results in a corresponding proximal translation of drive member 380a which is engaged with the drive screw 340a, clockwise rotation of the drive screw 340b results in a corresponding proximal translation of drive member 380b which is engaged with the drive screw 340b, and clockwise rotation of the drive screw 340c results in a corresponding proximal translation of drive member 380c which is engaged with the drive screw 340c. Additionally, for example, counterclockwise rotation of the drive screw 340a results in a corresponding distal translation of drive member 380a which is engaged with the drive screw 340a, counterclockwise rotation of the drive screw 340b results in a corresponding distal translation of drive member 380b which is engaged with the drive screw 340b, and counterclockwise rotation of the drive screw 340c results in a corresponding distal translation of drive member 380c which is engaged with the drive screw 340c.

Additionally, in one aspect, when one drive nut 350a, 350b, 350c, from a first drive assembly 300a, 300b, 300c, moves in a first longitudinal direction (e.g., proximally), it is envisioned that a different drive nut 350a, 350b, 350c, from a different drive assembly 300a, 300b, 300c, is forced to correspondingly move in a second, opposite longitudinal direction (e.g., distally). Such a function may be accomplished via the physical interaction between the individual drive assemblies 300a, 300b, 300c amongst each other or via control of the respective motors 52a, 52b, and 52c, as will be described in greater detail below. Such configurations function to, for example, compensate for any slack in the drive members 380a, 380b, 380c or to create a slack in drive members 380a, 380b, 380c. It is contemplated and in accordance with the present disclosure that each drive nut 350a, 350b, 350c may be independently driven.

As discussed above, each of the motors 52a, 52b, and 52c may be controlled in a corresponding manner to negate slack formation in any of drive members 380a, 380b, 380c, when another one of drive members 380a, 380b, or 380c (e.g., an opposing drive member) is translated in an opposing direction. Additionally, each of the motors 52a, 52b, and 52c may be controlled in a corresponding manner to create slack in any of drive members 380a, 380b, 380c, when another one of drive members 380a, 380b, or 380c (e.g., an opposing drive member) is translated in an opposing direction. Such corresponding control of the motors 52a, 52b, 52c ensures that the proximal translation of any of drive members 380a, 380b, or 380c is not hindered by the stationary position of an opposing drive member 380a, 380b, or 380c. For example, when motor 52c is actuated to cause proximal translation of drive nut 350c (thereby translating drive member 380c in a proximal direction), motors 52a and 52b are coordinated with motor 52c to actuate in an opposite direction to cause distal translation of respective drive nuts 350a and 350b (thereby enabling drive members 380a and 380b to be moved in a distal direction when effectively pulled in a distal direction by the opposing force of drive member 380c). Additionally, for example, when motors 52a and 52b are actuated to cause proximal translation of respective drive nuts 350a and 350b (thereby translating respective drive members 380a and 380b in a proximal direction), motor 52c is coordinated with motors 52a and 52b to actuate in an opposite direction to cause distal translation of drive nut 350c (thereby enabling drive member 380c to be moved in a distal direction when effectively pulled in a distal direction by the opposing force of drive member 380c). Additionally, for example, when motor 52a is actuated to cause proximal translation of drive nut 350a (thereby translating drive member 380a in a proximal direction), motor 52b may be coordinated with motor 52a to actuate in an opposite direction to cause distal translation of drive nut 350b (thereby enabling drive member 380b to be moved in a distal direction when effectively pulled in a distal direction by the opposing force of drive member 380a), and vice versa.

Reference may be made to U.S. Pat. No. 8,828,023, filed on Nov. 3, 2011, entitled "Medical Workstation," the entire content of which is incorporated herein by reference, for a detailed discussion of the construction and operation of medical work station 1. Additionally, reference may be made to commonly owned International Patent Application No. PCT/US14/61329, filed on Oct. 20, 2014 entitled "Wrist and Jaw Assemblies for Robotic Surgical Systems," the entire contents of which are incorporated herein by reference, for a detailed discussion of illustrative examples of the construction and operation of end effectors for use with or connection to electromechanical surgical instrument 200.

Referring now to FIGS. 6-23, an end effector of electromechanical surgical instrument 200 for connection to robot arms 2, 3 and for manipulation by control device 4, will be described and is generally designated as end effector 1000. As described above, end effector 1000 is disposed at a distal portion of electromechanical surgical instrument 200. In one aspect, end effector 1000 may be removably coupled to the distal portion of electromechanical surgical instrument 200 such that a variety of interchangeable end effectors may be used with electromechanical surgical instrument 200. In another aspect, end effector 1000 is fixed and non-removable from the distal portion of the electromechanical surgical instrument.

End effector 1000 is composed of a wrist assembly 1100 and a medical instrument or surgical tool "T." The wrist assembly 1100 is configured to articulate such that the instrument or surgical tool "T" may be positioned or moved by control device 4 (FIG. 1). Surgical tool "T" may be a monopolar electrosurgical device (for example, monopolar tool 150) electrically coupled to an electrosurgical generator 10 (FIG. 1) via power cable 118. In certain configurations, a return pad (not shown) may be required which couples a portion of the patient table "ST" or the patient "P" to the electrosurgical generator 10 creating a return path to the electrosurgical generator 10.

Electrosurgical generator 10 is configured to generate electrosurgical radio frequency energy and transmit the generated electrosurgical radio frequency energy to monopolar tool 150 of end effector 1000 for treatment of tissue via power cable 118. It is contemplated that generators such as those sold by Covidien, a division of Medtronic, may be used as a source of electrosurgical energy (electrosurgical generator 10), e.g., Ligasure® Generator, FORCE EZ® Electrosurgical Generator, FORCE FX® Electrosurgical Generator, FORCE 1C™, FORCE 2™ Generator, SurgiStat® II, FORCETRIAD®, VALLEYLAB™ FT10 Energy Platform, and the FORCETRIAD™ Energy Platform electrosurgical generators or other envisioned generators which may perform different or enhanced functions. One such system is described in commonly-owned U.S. Pat. No. 6,033,399, filed on Apr. 9, 1997, entitled "ELECTROSURGICAL GENERATOR WITH ADAPTIVE POWER CONTROL," the entire content of which is incorporated by reference herein. Further details regarding electrosurgical generator 10 may also be found in U.S. Pat. No. 7,648,499, filed on Mar. 21, 2006, entitled "SYSTEM AND METHOD FOR GENERATING RADIO FREQUENCY ENERGY," the entire content of which is incorporated by reference herein.

Wrist assembly 1110 of end effector 1000 includes a proximal hub 112, in the form of a distally extending clevis, defining a first longitudinal axis "X1-X1." Proximal hub 112 defines a first pivot axis "A-A" that is oriented orthogonal to the first longitudinal axis "X1-X1." In an embodiment, first pivot axis "A-A" may extend through the first longitudinal axis "X1-X1." Proximal hub 112, being in the form of a clevis, includes a pair of spaced apart, opposed upright supports 112a, 112b, a proximal pulley pin 112c, and a distal pulley pin 112d through which first pivot axis "A-A" extends.

Figure 19:
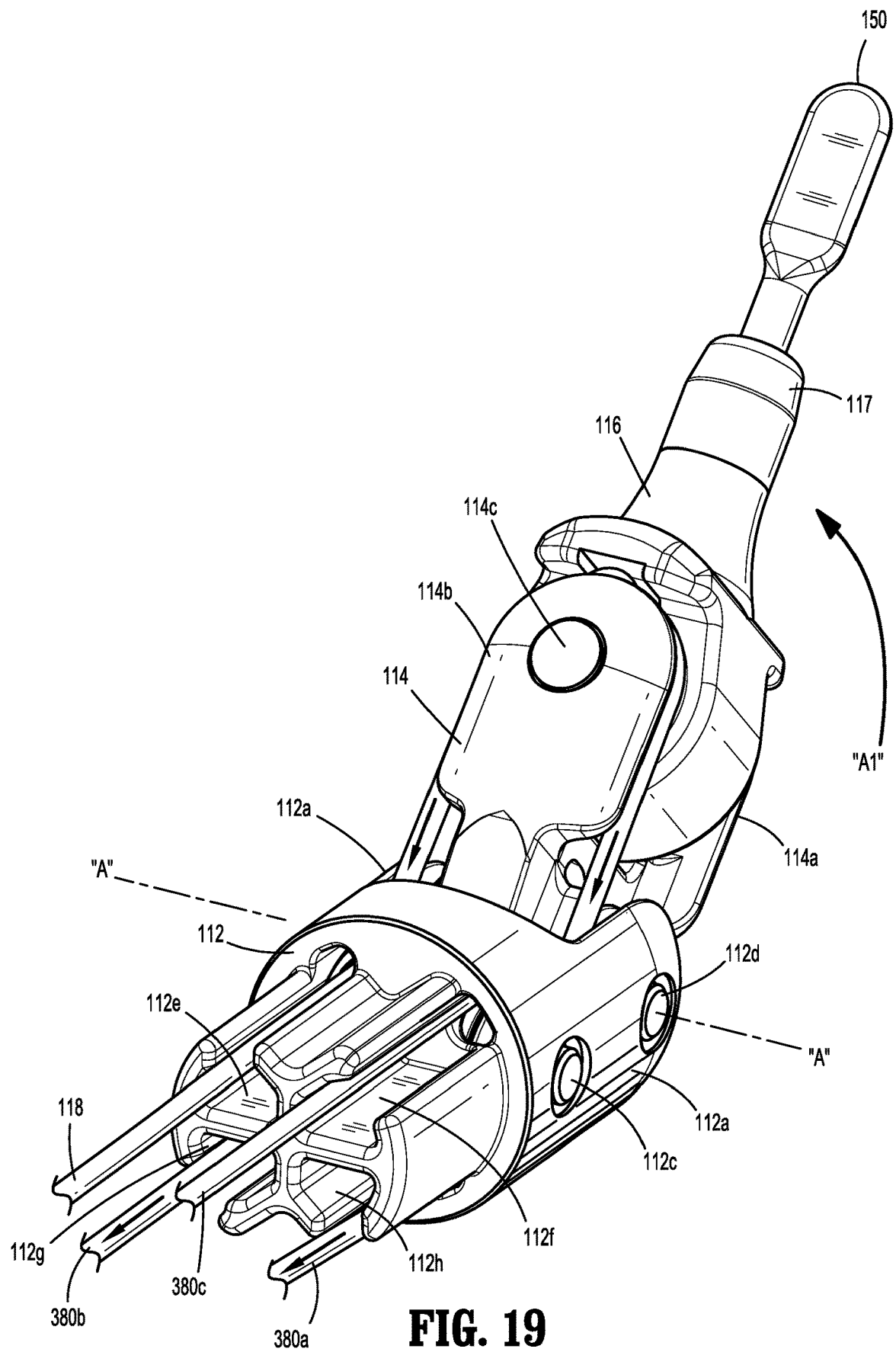
FIG. 19 is a rear, perspective view of the end effector of FIG. 6, with parts removed, illustrating the pulley system thereof and illustrating a wrist assembly thereof in an articulated condition.
Figure 20:
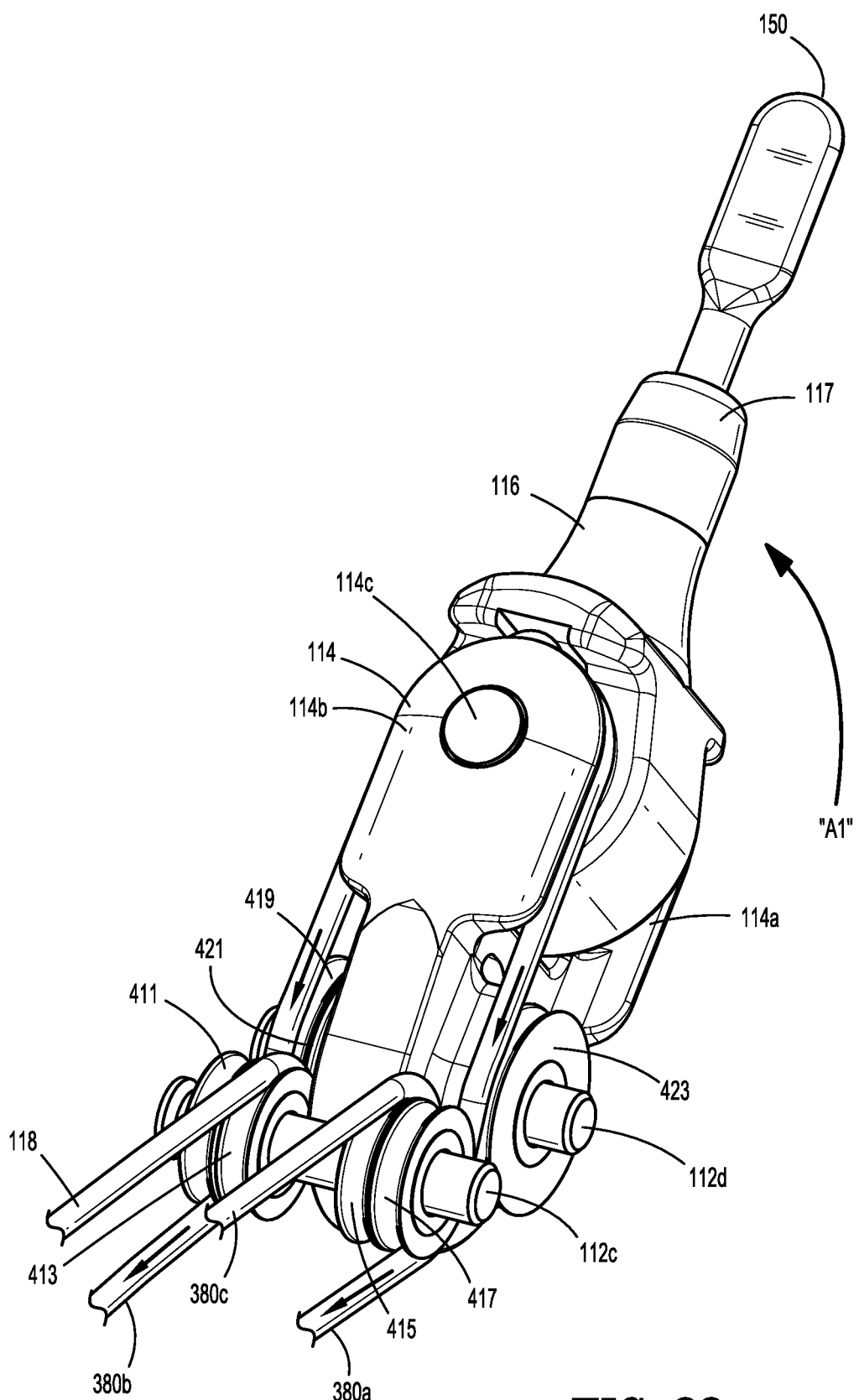
FIG. 20 is a rear, perspective view of the end effector of FIG. 6, with parts removed, illustrating the pulley system thereof and illustrating the wrist assembly thereof in an articulated condition.

Briefly referring specifically to FIG. 19, in one configuration, proximal hub 112 defines channels 112e, 112f, 112g, 112h for the passage of respective drive members 380a, 380b, 380c, and power cable 118 therethrough. For example, drive member 380a may be passed through channel 112h of proximal hub 112, drive member 380b may be passed through channel 112g of proximal hub 112, drive member 380c may be passed through channel 112f of proximal hub 112, and power cable 118 may be passed through channel 112e of proximal hub 112.

Wrist assembly 1100 further includes a distal hub 114 pivotally connected to upright supports 112a, 112b of proximal hub 112 via the distal pulley pin 112d. In particular a proximal portion of the distal hub 114 is pivotally coupled to the opposed upright supports 112a, 112b of the proximal hub 112 via the distal pulley pin 112d. In this regard, distal hub 114 may pivot relative to proximal hub 112 about first pivot axis "A-A." Distal hub 114 may be in the form of a distally extending clevis and defines a second longitudinal axis "X2-X2." Distal hub 114 defines a second pivot axis "B-B" that is oriented orthogonal to the second longitudinal axis "X2-X2." In an embodiment, when the first longitudinal axis "X1-X1" is parallel with the second longitudinal axis "X2-X2" (e.g., electromechanical surgical instrument 200 is in an axially aligned orientation), second pivot axis "B-B" may extend through first longitudinal axis "X1-X1" and the second longitudinal axis "X2-X2." Distal hub 114, being in the form of a clevis, includes a pair of spaced apart, opposed upright supports 114a, 114b, and a distal hub pin 114c through which second pivot axis "B-B" extends.

Wrist assembly 1100 further includes a support hub 116 pivotally connected to upright supports 114a, 114b of distal hub 114 via the distal hub pin 114c. In particular a proximal portion of the support hub 116 is pivotally coupled to the opposed upright supports 114a, 114b of the distal hub 114 via the distal hub pin 114c. Support hub 116 defines a third longitudinal axis "X3-X3" and pivots about the second pivot axis "B-B" defined by distal hub 114.

Support hub 116 is configured to be coupled to a monopolar tool 150. In one aspect, support hub 116 includes a monopolar tool 150. In another aspect, support hub 116 includes an opening 116a for selectively coupling the monopolar tool 150 to the support hub 116. Support hub 116 may also include a grommet 117 adjacent the opening 116a to support the monopolar tool 150 therein. Power cable 118 passes through support hub 116 to electrically couple the monopolar tool 150 to the electrosurgical generator 10 (FIG. 1).

Support hub 116 may additionally function as a protective heat shield to thermally separate the monopolar tool 150 from the remaining components of the end effector 1000. To this end, distal hub 114 and other components of the end effector 1000 are protected from thermal damage during activation and use of monopolar tool 150. In one aspect, support hub 116 may be formed of a non-conducting, high temperature material (for example, ceramic) to separate the monopolar tool 150 from other components of the end effector 1000 (such as distal hub 114 and/or proximal hub 112). Such a configuration displaces the arc point a distance away from the proximate components of the end effector 1000, limiting the amount of potential thermal damage during use or discharge of the monopolar tool 150.

Grommet 117 may additionally function as a protective heat shield to thermally separate the monopolar tool 150 from the remaining components of the end effector 1000. To this end, support hub 116 and other components of the end effector 1000 are protected from thermal damage during activation and use of monopolar tool 150. In one aspect, grommet 117 may be formed of a non-conducting, high temperature material (for example, ceramic) to separate the monopolar tool 150 from other components of the end effector 1000 (such as support hub 116, distal hub 114, and/or proximal hub 112). Such a configuration displaces the arc point a distance away from the proximate components of the end effector 1000, limiting the amount of potential thermal damage during use or discharge of the monopolar tool 150.

Monopolar tool 150 may be a powered electrode or a non-powered instrument. In certain embodiments, monopolar tool 150 is in the form of a blade having at least one sharpened edge. Alternatively, monopolar tool 150 may have rounded edges and a rounded distal tip to assist in facilitating atraumatic movement of tissue.

In a configuration where monopolar tool 150 is an electrode, monopolar tool 150 may be used to coagulate, cut, and/or seal tissue. The monopolar tool 150 electrode is an electrically conducting element which may be elongated and may be in the form of a thin flat blade with a pointed or rounded distal end. Alternatively, the electrode may include an elongated narrow cylindrical needle which is solid or hollow with a flat, rounded, pointed or slanted distal end. Monopolar tool 150 may be configured to transmit radio frequency energy generated by the electrosurgical generator 10 (FIG. 1).

Continuing with reference to FIGS. 6-23, wrist assembly 1100 of end effector 1000 includes pulley system 400. Pulley system 400 includes pulleys 411, 413, 415, 417, 419, 421, 423 disposed between upright supports 112a, 112b of proximal hub 112. In particular, in an assembled configuration, pulleys 411, 413, 415, 417 are coupled to upright supports 112a, 112b of proximal hub 112 via proximal pulley pin 112c such that pulleys 411, 413, 415, 417 may spin about proximal pulley pin 112c. In one configuration, pulleys 411, 413 are disposed on one side of a proximal portion of distal hub 114 and pulleys 415, 417 are disposed on the other side of the proximal portion of distal hub 114. Additionally, pulleys 419, 421, 423 are coupled to upright supports 112a, 112b of proximal hub 112 via distal pulley pin 112d such that pulleys 419, 421, 423 may spin about distal pulley pin 112d. In one configuration, pulleys 419, 421 are disposed on one side of a proximal portion of distal hub 114 and pulley 423 is disposed on the other side of the proximal portion of distal hub 114.

Power cable 118, which electrically couples the monopolar tool 150 to the electrosurgical generator 10 (FIG. 1), extends through channel 112e of proximal hub 112, around a portion of pulley 413, around a portion of pulley 421, and through the support hub 116 to electrically couple to the monopolar tool 150. In one aspect, a distal portion of power cable 118 is permanently coupled to the monopolar tool 150. For example, monopolar tool 150 may have a hole drilled into its proximal end and a distal end of the power cable 118 may be inserted into the hole and permanently coupled to the monopolar tool 150. Such a permanent coupling may be achieved by, for example, laser welding. This connection between the power cable 118 and the monopolar tool 150 may be achieved prior to assembly of the support hub 116. To this end, power cable 118 may be fed proximally into the support hub 116 through opening 116a and through the remaining components of end effector 1000.

Alternatively, in an interchangeable configuration, power cable 118 may be removably coupled to the monopolar tool 150 such that different monopolar tools 150 may be used interchangeably. For example, a distal portion of the power cable 118 may include a coupling structure configured to correspondingly mate with a proximal portion of the monopolar tool 150, thereby enabling selective coupling and removal of interchangeable monopolar tools 150.

A proximal portion of the power cable 118 includes a connector (not shown) for connecting the power cable 118 to generator 10. The connector may include identification elements (e.g., RFID tag, bar code, or read-only or read/write memory chips) which may be read by generator 10 to provide identification information of the type of monopolar tool 150 and/or the usage details of the monopolar tool 150.

In order to prevent mechanical stress imparted on the power cable 118 and to manage the position of the power cable 118 within the components of the end effector 1000 during movement and articulation of the end effector 1000, power cable 118 may include slack. The slack of the power cable 118 may be managed passively, for example, via a service loop used in combination with a return spring.

Drive member 380c extends from a proximal portion of the electromechanical surgical instrument 200 to the end effector 1000. As described above, a proximal end 380cp (FIG. 4) of drive member 380c is operably coupled to drive nut 350c. Drive member 380c extends through channel 112f of proximal hub 112, around a portion of pulley 415 and around a protruding surface 114g (FIG. 14) of distal hub 114. Protruding surface 114g is axially aligned with pulleys 419, 421, 423 and distal pulley pin 112d. A distal end 380cd of drive member 380c is coupled to a portion of the distal hub 114 such that proximal movement of the drive member 380c causes corresponding rotation of the distal hub 114 about axis "A-A." Distal end 380cd of drive member 380c is coupled to distal hub 114 at a point which is distal to the distal pulley pin 112d to enable rotation of distal hub 114 about axis "A-A." In one configuration, distal end 380cd of drive member 380c passes through an aperture formed in distal hub 114. Distal end 380cd of drive member 380c may be coupled to distal hub 114 via adhesive, glue, welding, snap-fitting or any other accepted means.

Figure 11:
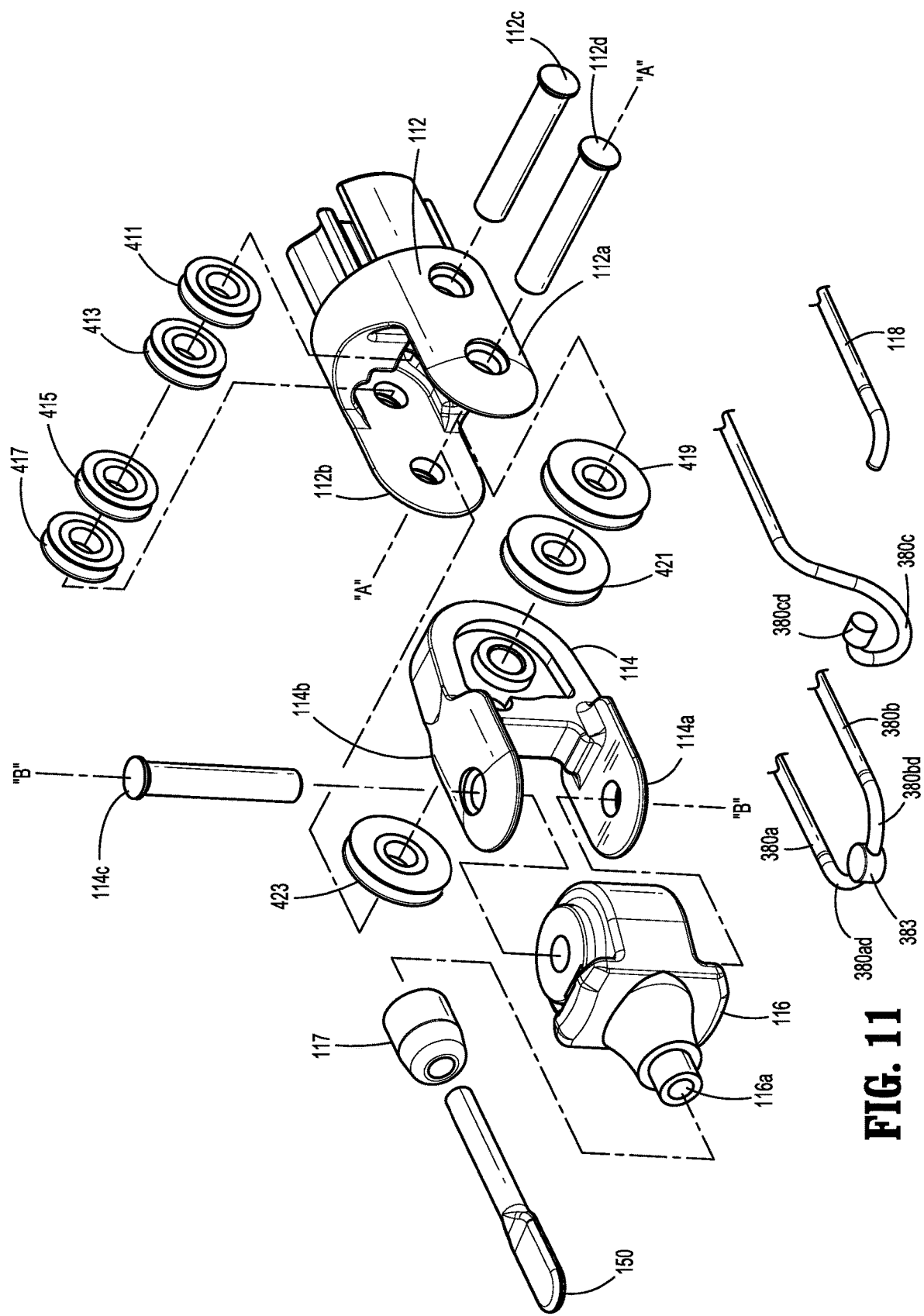
FIG. 11 is a perspective view, with parts separated, of the end effector of FIG. 6.

With reference to FIGS. 11, 17, and 18, drive members 380a and 380b will now be discussed. Drive member 380a and drive member 380b extend from a proximal portion of the electromechanical surgical instrument 200 to the end effector 1000. As described above, a proximal end 380ap (FIG. 4) of drive member 380a is operably coupled to drive nut 350a and a proximal end 380bp of drive member 380b if operably coupled to drive nut 350b. A distal end 380ad of drive member 380a connects to a distal end 380bd of drive member 380b via an engagement member 383.

Figure 12:
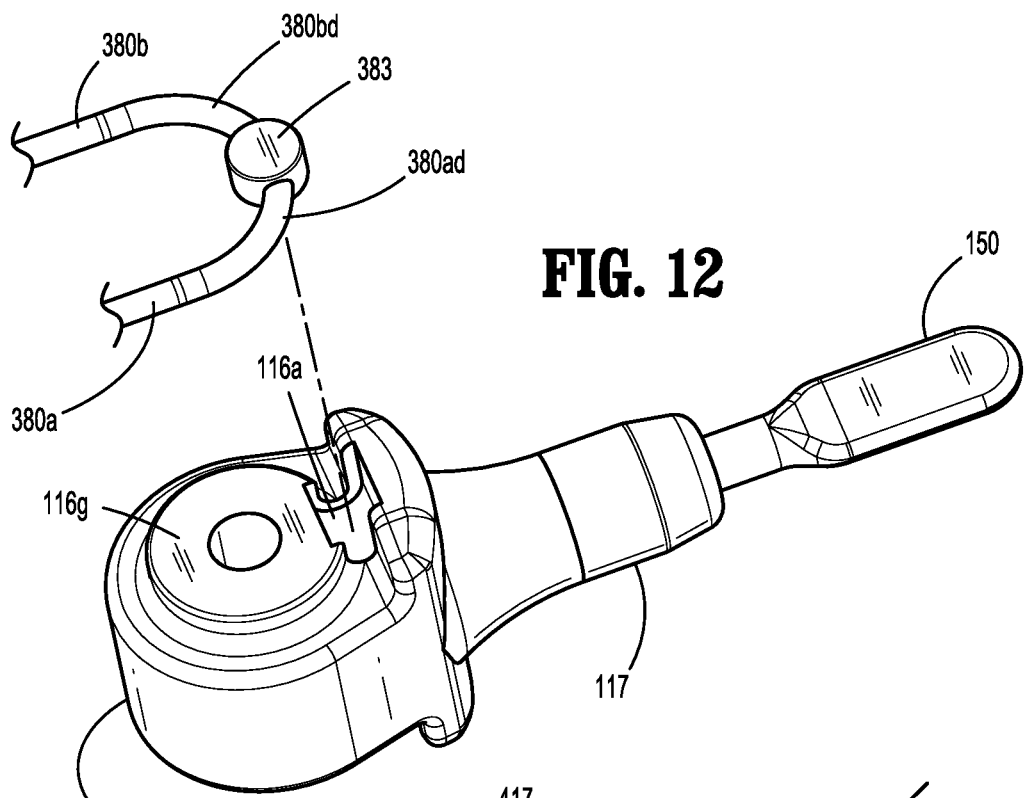
FIG. 12 is a perspective view of a support hub of the end effector of FIG. 6.
Figure 13:
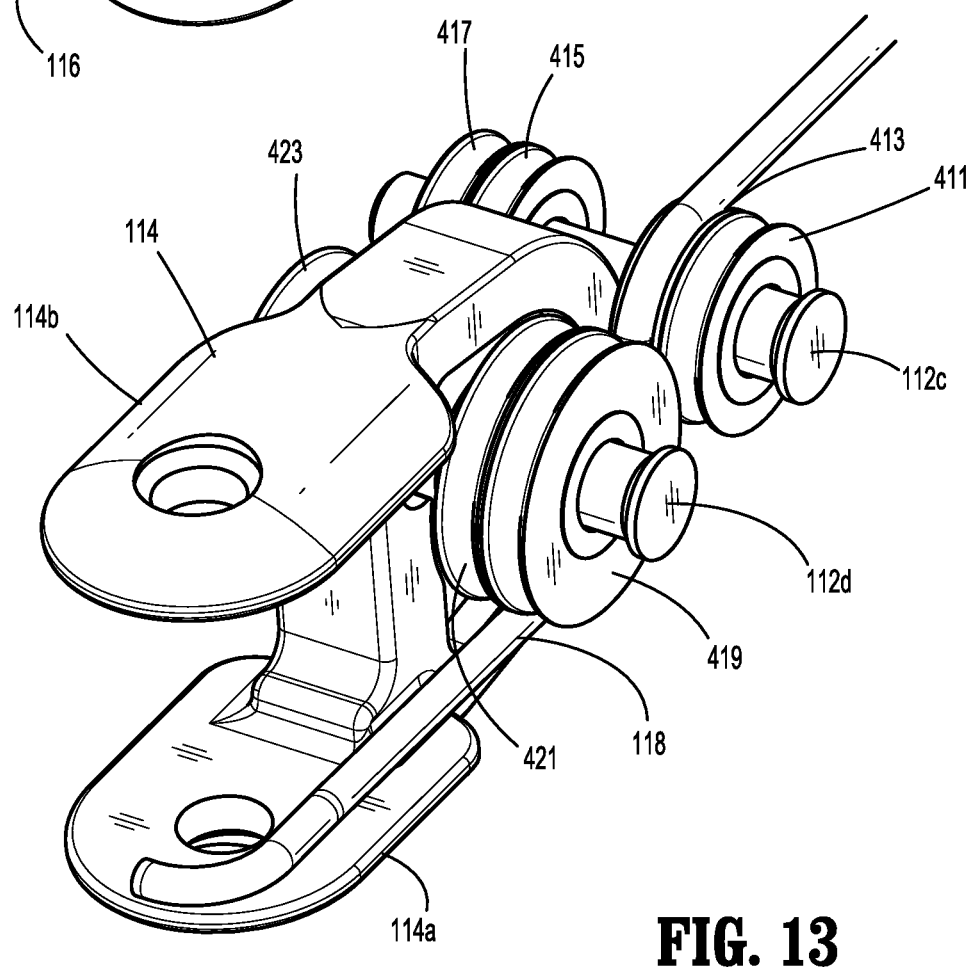
FIG. 13 is a perspective view of a distal hub and pulley system of the end effector of FIG. 6.
Figure 14:
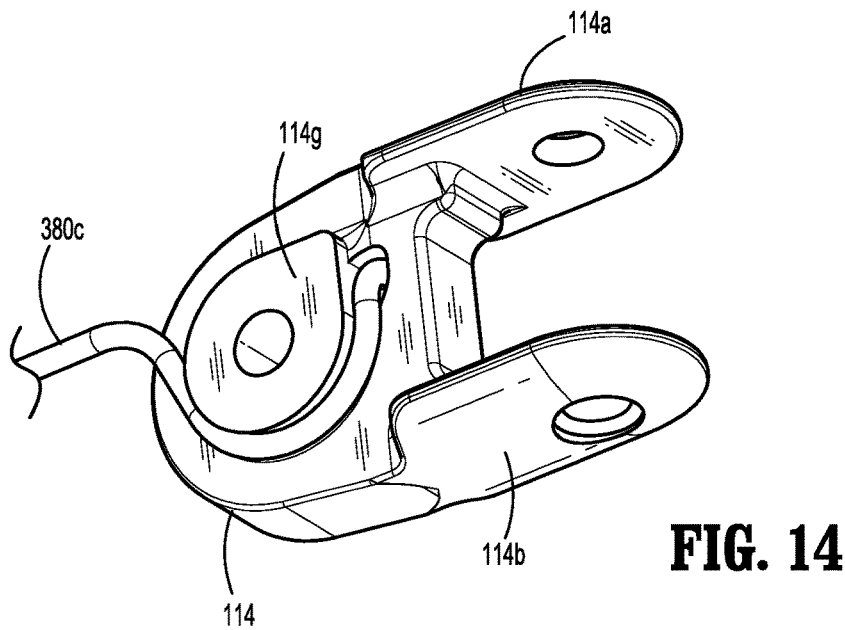
FIG. 14 is a perspective view of the distal hub of the end effector of FIG. 6.
Figure 15:
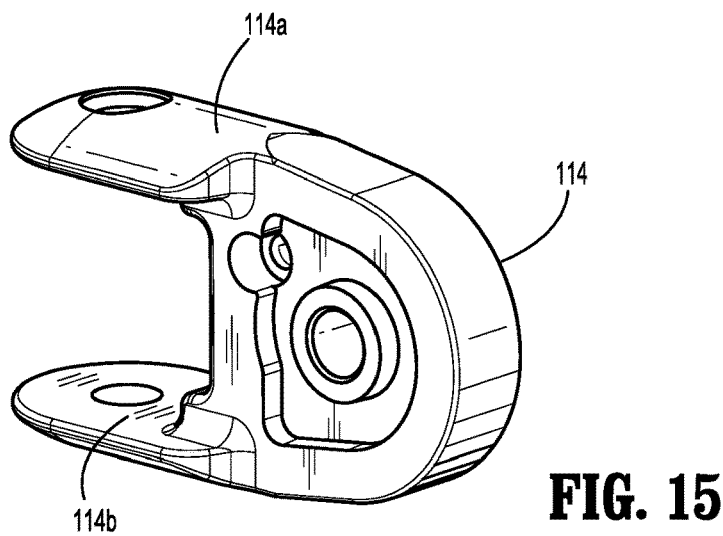
FIG. 15 is another perspective view of the distal hub of the end effector of FIG. 6.
Figure 16:
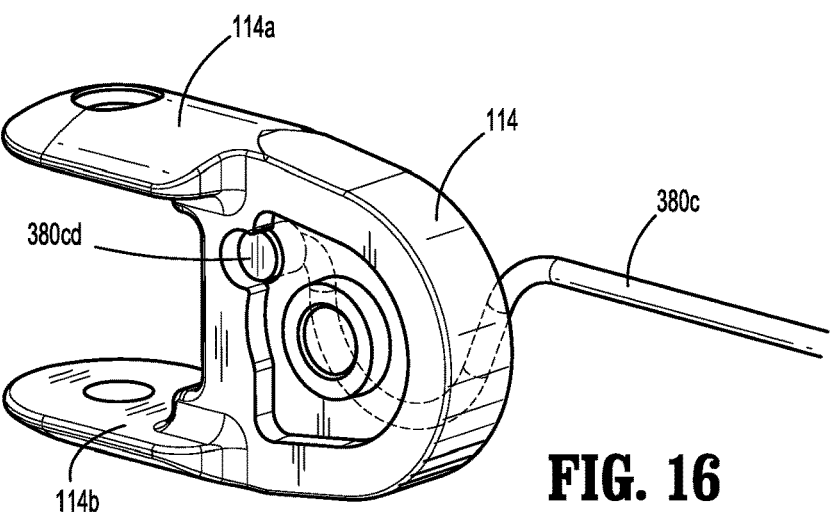
FIG. 16 is a further perspective view of the distal hub of the end effector of FIG. 6.

Drive member 380a extends through channel 112h of proximal hub 112, around a portion of pulley 417, around a portion of pulley 423 and around a first side of protruding surface 116g of support hub 116 (FIG. 12). Meanwhile, drive member 380b extends through channel 112g of proximal hub 112, around a portion of pulley 411, around a portion of pulley 419 and around a second side of protruding surface 116g of support hub 116 (FIG. 12). The distal ends 380ad, 380bd of respective drive members 380a, 380b are coupled to a portion of support hub 116 via engagement member 383. In one configuration, engagement member 383 is fixed to a notch 116n of support hub 116 such that movement of drive member 380a and/or drive member 380b causes corresponding movement of support hub 116.

Although drive member 380a and drive member 380b are illustrated and described as two separate drive members, drive member 380a may be a first half or side of a unitary drive member and drive member 380b may be a second half or side of the same unitary drive member. That is, in one configuration, drive members 380a and 380b form a single cable that is at least partially wrapped around protruding surface 116g of support hub 116 and secured to at least a point thereof, or a single cable which may be wrapped at least once around protruding surface 116g or any portion of support hub 116 in the manner of a capstan. In a configuration where drive member 380a and drive member 380b are two sides of a single unitary cable, the single unitary cable extends distally through channel 112g of proximal hub 112, around a portion of pulley 411, around a portion of pulley 419, around a portion of protruding surface 116g of support hub 116 and proximally around a portion of pulley 423, around a portion of pulley 417, and through channel 112h of proximal hub 112. A proximal end of the single unitary cable is operably coupled to drive nut 350a (FIG. 5) and a distal end of the single unitary cable is operably coupled to drive nut 350b (FIG. 5). In addition to wrapping around protruding surface 116g, the single unitary cable is coupled to support hub 116 at a midpoint of the single unitary cable via engagement member 383 such that movement of either one or both sides of the single unitary cable causes corresponding movement of support hub 116.

In operation, as illustrated in FIGS. 19-23, end effector 1000 of electromechanical surgical instrument 200 is pivoted about a first pivot axis "A-A" (FIG. 19) and/or a second pivot axis "B-B" (FIGS. 21-23) of wrist assembly 1100, via movement of some or all of drive members 380a, 380b, 380c in a proximal or distal direction. Briefly referring back to FIGS. 2 and 3, each of drive members 380a, 380b, 380c is pulled proximally or advanced distally via activation of a respective motor 52a, 52b, 52c. For example, actuation of motor 52a causes corresponding rotation of drive screw 340a and rotation of drive screw 340a causes corresponding longitudinal movement or translation of drive nut 350a along a longitudinal axis defined by drive screw 340a. As proximal end 380ap of drive member 380a is coupled to drive screw 350a, longitudinal movement of drive screw 350a causes corresponding longitudinal movement of drive member 380a. Additionally, for example, coordinated actuation of motor 52b causes corresponding rotation of drive screw 340b and rotation of drive screw 340b causes corresponding longitudinal movement or translation of drive nut 350b along a longitudinal axis defined by drive screw 340b. As proximal end 380bp of drive member 380b is coupled to drive screw 350b, longitudinal movement of drive screw 350b causes corresponding longitudinal movement of drive member 380b. Additionally, for example, coordinated actuation of motor 52c causes corresponding rotation of drive screw 340c and rotation of drive screw 340c causes corresponding longitudinal movement or translation of drive nut 350c along a longitudinal axis defined by drive screw 340c. As proximal end 380cp of drive member 380c is coupled to drive screw 350c, longitudinal movement of drive screw 350c causes corresponding longitudinal movement of drive member 380c.

In operation, as illustrated in FIGS. 19-23, in order to pivot end effector 1000 of electromechanical surgical instrument 200 about first pivot axis "A-A" of wrist assembly 1100 in the direction of arrow "A1," it is contemplated that the proximal end 380ap of drive member 380a and the proximal end 380bp of drive member 380b are drawn in a proximal direction as a result of an input from control device 4 to activate both of motor 52a and motor 52b (FIG. 2B) in the same rotational direction. Simultaneous or coordinated activation of motor 52a, to which proximal end 380ap is operably coupled via drive assembly 300a, and motor 52b, to which proximal end 380bp is operably coupled via drive assembly 300b, in the same direction causes proximal movement of both of drive member 380a and drive member 380b thereby causing both of the distal hub 114 and the support hub 116 to articulate about axis "A-A" in the direction of arrow "A1." In addition to drawing both of drive member 380a and drive member 380b proximally via simultaneous activation of motor 52a and 52b in the same rotational direction, drive member 380c is advanced distally via coordinated activation of motor 52c, to which proximal end 380cp of drive member 380c is operably coupled via drive assembly 300c.

Figure 21:
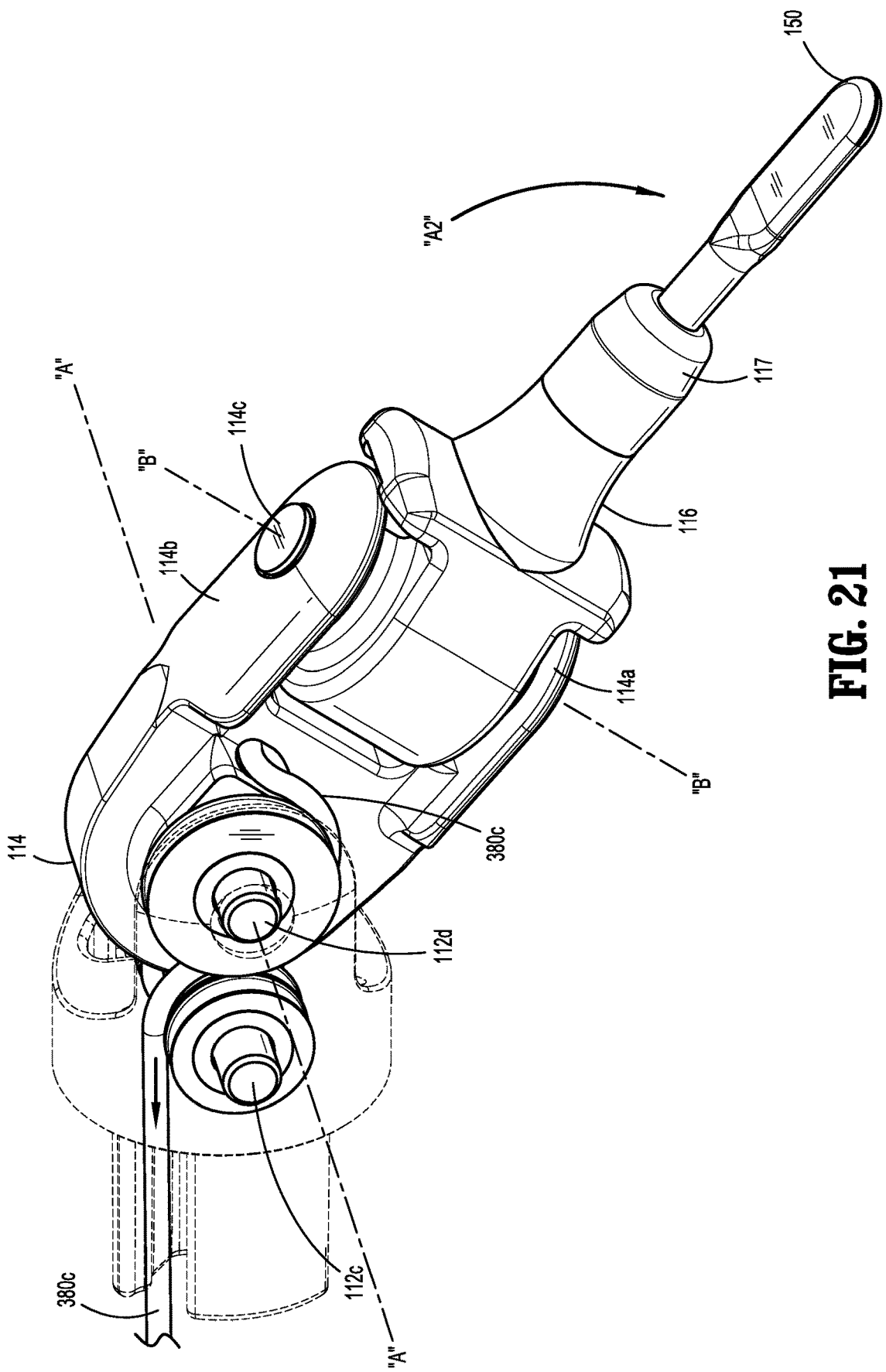
FIG. 21 is a side, perspective view of the end effector of FIG. 6, with parts removed, illustrating the wrist assembly thereof in another articulated condition.

Referring specifically to FIG. 21, in order to pivot end effector 1000 of electromechanical surgical instrument 200 about first pivot axis "A-A" of wrist assembly 1100 in the direction of arrow "A2," which is opposite the direction of arrow "A1," it is contemplated that the proximal end 380cp of drive member 380c is drawn in a proximal direction as a result of an input from control device 4 to activate motor 52c, to drive member 380c is connected via drive assembly 300c. In addition to drawing drive member 380c proximally via coordinated activation of motor 52c, both drive member 380a and 380b are advanced distally via simultaneous coordinated activation of motor 52a, to which drive member 380a is coupled via drive assembly 300a, and motor 52b, to which drive member 380b is coupled via drive assembly 300c, in the same direction.

Additionally, in operation, as illustrated in FIGS. 22 and 22, in order to pivot support hub 116 of end effector 1000 about second pivot axis "B-B" of wrist assembly 1100, it is contemplated that one of drive member 380a and drive member 380b are drawn in opposite directions as a result of an input from control device 4 to activate a motor 52a in one direction and activate motor 52b in opposite directions. That is, in order to pivot support hub 116 about pivot axis "B-B" in the direction of arrow "B1," (FIG. 22) drive member 380a is pulled proximally via activation of motor 52a, while drive member 380b is advanced distally via simultaneous coordinated activation of motor 52b in the opposite direction. Additionally, in order to pivot support hub 116 about pivot axis "B-B" in the direction of arrow "B2," (FIG. 23) drive member 380a is advanced distally via activation of a motor 52a while drive member 380b is pulled proximally via simultaneous coordinated activation of motor 52b in the opposite direction.

It will be understood that various modifications may be made to the embodiments disclosed herein. For example, while the cables disclosed herein have been shown and described as being connected to specific portions of the distal hub and support hub, it is contemplated and within the scope of the present disclosure, for the cables to be operatively connected to any portion of the hubs or supports. Therefore, the above description should not be construed as limiting, but merely as exemplifications of various embodiments. Those skilled in the art will envision other modifications within the scope and spirit of the claims appended thereto.

What is claimed is:

1. An end effector for use with a robotic system, the end effector comprising:
   a proximal hub defining a first pivot axis;
   a distal hub pivotally coupled to the proximal hub about the first pivot axis, the distal hub defining a second pivot axis transverse to the first pivot axis;
   a support hub pivotally coupled to the distal hub about the second pivot axis, the support hub including an electrosurgical tool;
   a first drive member and a second drive member operably coupled to the support hub; and
   a third drive member operably coupled to the distal hub, wherein:
      simultaneous proximal translation of the first drive member and the second drive member causes the distal hub to pivot about the first pivot axis; and
      proximal translation of only one of the first drive member or the second drive member causes the support hub to pivot about the second pivot axis.

2. The end effector according to claim 1, wherein:
   simultaneous proximal translation of the first drive member and the second drive member causes the distal hub to pivot about the first pivot axis in a first direction; and proximal translation of the third drive member causes the distal hub to pivot about the first pivot axis in a second direction opposite the first direction.

3. The end effector according to claim 1, wherein:
proximal translation of the first drive member and distal translation of the second drive member cause the support hub to pivot about the second pivot axis in a first direction; and
distal translation of the first drive member and proximal translation of the second drive member cause the support hub to pivot about the second pivot axis in a second direction opposite the first direction.

4. The end effector according to claim 1, further comprising a power cable electrically coupled to the electrosurgical tool and configured to electrically couple the electrosurgical tool to an electrosurgical generator.

5. The end effector according to claim 1, further comprising a first pulley, a second pulley, a third pulley, and a fourth pulley, each of the first pulley, second pulley, third pulley, and fourth pulley operably coupled to the proximal hub via a proximal pulley pin and rotatable along the first pivot axis, wherein the first drive member wraps around at least a portion of the first pulley, the second drive member wraps around at least a portion of the second pulley, and the third drive member wraps around at least a portion of the third pulley.

6. The end effector according to claim 5, further comprising a fifth pulley, a sixth pulley, and a seventh pulley, each of the fifth pulley, the sixth pulley, and the seventh pulley operably coupled to the proximal hub via a distal pulley pin, wherein the first drive member wraps around at least a portion of the fifth pulley, and the second drive member wraps around at least a portion of the sixth pulley.

7. An electromechanical surgical instrument for use with a robotic system, the electromechanical surgical instrument comprising:
a drive assembly; and
an end effector operably coupled to the drive assembly, the end effector comprising:
a proximal hub defining a first pivot axis;
a distal hub pivotally coupled to the proximal hub about the first pivot axis, the distal hub defining a second pivot axis transverse to the first pivot axis;
a support hub pivotally coupled to the distal hub about the second pivot axis and including an electrosurgical tool;
a first drive member, wherein a distal portion of the first drive member is coupled to the support hub;
a second drive member, wherein a distal portion of the second drive member is coupled to the support hub; and
a third drive member, wherein a distal portion of the third drive member is coupled to the distal hub;
wherein:
simultaneous proximal translation of the first drive member and the second drive member causes the distal hub to pivot about the first pivot axis; and
proximal translation of only one of the first drive member or the second drive member causes the support hub to pivot about the second pivot axis.

8. The electromechanical surgical instrument according to claim 7, wherein:
simultaneous proximal translation of the first drive member and the second drive member causes the distal hub to pivot about the first pivot axis in a first direction; and
proximal translation of the third drive member causes the distal hub to pivot about the first pivot axis in a second direction opposite the first direction.

9. The electromechanical surgical instrument according to claim 7, wherein:
proximal translation of the first drive member and distal translation of the second drive member cause the support hub to pivot about the second pivot axis in a first direction; and
distal translation of the first drive member and proximal translation of the second drive member cause the support hub to pivot about the second pivot axis in a second direction opposite the first direction.

10. The electromechanical surgical instrument according to claim 7, further comprising a power cable electrically coupled to the electrosurgical tool and configured to electrically couple the electrosurgical tool to an electrosurgical generator.

11. The electromechanical surgical instrument according to claim 7, further comprising a first pulley, a second pulley, a third pulley, and a fourth pulley, each of the first pulley, second pulley, third pulley, and fourth pulley operably coupled to the proximal hub via a proximal pulley pin and rotatable along the first pivot axis, wherein the first drive member wraps around at least a portion of the first pulley, the second drive member wraps around at least a portion of the second pulley, and the third drive member wraps around at least a portion of the third pulley.

12. The electromechanical surgical instrument according to claim 7, further comprising:
a fifth pulley, a sixth pulley, and a seventh pulley, each of the fifth pulley, the sixth pulley, and the seventh pulley operably coupled to the proximal hub via a distal pulley pin, wherein the first drive member wraps around at least a portion of the fifth pulley, and the second drive member wraps around at least a portion of the sixth pulley.

13. A robotic electrosurgical system comprising:
an electrosurgical generator configured to generate electrosurgical energy; and
an electromechanical surgical instrument having an electrosurgical tool configured to couple to the electrosurgical generator and transmit the generated electrosurgical energy, the electromechanical surgical instrument comprising:
a proximal hub defining a first pivot axis;
a distal hub pivotally coupled to the proximal hub about the first pivot axis, the distal hub defining a second pivot axis transverse to the first pivot axis;
a support hub pivotally coupled to the distal hub about the second pivot axis and including the electrosurgical tool;
a first drive member, wherein a distal portion of the first drive member is coupled to the support hub;
a second drive member, wherein a distal portion of the second drive member is coupled to the support hub; and
a third drive member, wherein a distal portion of the third drive member is coupled to the distal hub;
wherein:
simultaneous proximal translation of the first drive member and the second drive member causes the distal hub to pivot about the first pivot axis; and
proximal translation of only one of the first drive member or the second drive member causes the support hub to pivot about the second pivot axis.

14. The robotic electrosurgical system according to claim 13, further comprising:
   a first motor configured to actuate the first drive member;
   a second motor configured to actuate the second drive member;
   a third motor configured to actuate the third drive member; and
   a control device configured to control actuation of at least one of the first motor, the second motor, or the third motor.

15. The robotic electrosurgical system according to claim 14, wherein the control device is configured to coordinate control of the first motor with control of the second motor by actuating the first motor in a first direction when actuating the second motor in a second direction opposite the first direction.

16. The robotic electrosurgical system according to claim 14, wherein the control device is configured to coordinate control of the first motor and the second motor with control of the third motor by actuating the first motor and the second motor in a first direction when actuating the third motor in a second direction opposite the first direction.

17. The robotic electrosurgical system according to claim 13, wherein:
   simultaneous proximal translation of the first drive member and the second drive member causes the distal hub to pivot about the first pivot axis in a first direction; and
   proximal translation of the third drive member causes the distal hub to pivot about the first pivot axis in a second direction opposite the first direction.

18. The robotic electrosurgical system according to claim 13, further comprising:
   a power cable electrically coupling the electrosurgical tool to the electrosurgical generator.

* * * * *